US012412351B2

(12) United States Patent
Lee et al.

(10) Patent No.: US 12,412,351 B2
(45) Date of Patent: Sep. 9, 2025

(54) THREE-DIMENSIONAL DATA ACQUISITION METHOD AND DEVICE, AND COMPUTER-READABLE STORAGE MEDIUM STORING PROGRAM FOR PERFORMING SAME METHOD

(71) Applicant: MEDIT CORP., Seoul (KR)

(72) Inventors: Dong Hoon Lee, Seoul (KR); Han Sol Kim, Seoul (KR)

(73) Assignee: MEDIT CORP., Seoul (KR)

( * ) Notice: Subject to any disclaimer, the term of this patent is extended or adjusted under 35 U.S.C. 154(b) by 281 days.

(21) Appl. No.: 18/000,080

(22) PCT Filed: May 28, 2021

(86) PCT No.: PCT/KR2021/006694
§ 371 (c)(1),
(2) Date: Nov. 28, 2022

(87) PCT Pub. No.: WO2021/242053
PCT Pub. Date: Dec. 2, 2021

(65) Prior Publication Data
US 2023/0215122 A1     Jul. 6, 2023

(30) Foreign Application Priority Data

May 29, 2020   (KR) ................ 10-2020-0065388

(51) Int. Cl.
   *G06T 19/20*   (2011.01)
   *A61C 9/00*    (2006.01)
   (Continued)

(52) U.S. Cl.
   CPC ............ *G06T 19/20* (2013.01); *A61C 9/0053* (2013.01); *A61C 13/0004* (2013.01);
   (Continued)

(58) Field of Classification Search
   None
   See application file for complete search history.

(56) References Cited

U.S. PATENT DOCUMENTS 6,647,146 B1 * 11/2003 Davison ................. G06T 7/564
                                                             358/1.9
6,677,982 B1 *  1/2004 Chen .................... H04N 13/106
                                                             348/36
(Continued)

FOREIGN PATENT DOCUMENTS

JP    2003-532125 A   10/2003
JP    2005-80989 A     3/2005
(Continued)

OTHER PUBLICATIONS

Korean Office Action for Korean Application No. 10-2020-0065388 dated Jan. 14, 2022, 10 pages.
(Continued)

*Primary Examiner* — Jason A Pringle-Parker
(74) *Attorney, Agent, or Firm* — Sughrue Mion, PLLC

(57) ABSTRACT

A method of obtaining three-dimensional data includes: obtaining three-dimensional reference data with respect to an object; aligning, on the three-dimensional reference data, a first frame obtained by scanning a first region of the object; aligning, on the three-dimensional reference data, a second frame obtained by scanning a second region of the object, at least a portion of the second region overlapping the first region; and obtaining the three-dimensional data by merging the first frame with the second frame based on an overlapping portion between the first region and the second region.

18 Claims, 17 Drawing Sheets

(51) Int. Cl.
*A61C 13/00* (2006.01)
*A61C 13/34* (2006.01)
*G05B 19/4097* (2006.01)
*G06T 7/11* (2017.01)

(52) U.S. Cl.
CPC .......... *A61C 13/34* (2013.01); *G05B 19/4097* (2013.01); *G06T 7/11* (2017.01); *G05B 2219/35012* (2013.01); *G06T 2207/10081* (2013.01); *G06T 2207/10088* (2013.01); *G06T 2207/20221* (2013.01); *G06T 2207/30036* (2013.01); *G06T 2210/41* (2013.01); *G06T 2219/2004* (2013.01); *G06T 2219/2021* (2013.01)

(56) References Cited

U.S. PATENT DOCUMENTS

| | | | |
|---|---|---|---|
| 6,744,914 | B1 | 6/2004 | Rubbert et al. |
| 7,580,952 | B2* | 8/2009 | Logan .................... G06F 16/58 707/999.102 |
| 8,363,930 | B1 | 1/2013 | Francis, Jr. et al. |
| 9,036,881 | B2 | 5/2015 | Carlson et al. |
| 11,039,905 | B2 | 6/2021 | Je et al. |
| 2002/0154812 | A1* | 10/2002 | Chen ..................... G06T 3/4038 348/E13.008 |
| 2003/0066949 | A1* | 4/2003 | Mueller ............... H04N 13/254 348/E13.016 |
| 2003/0169913 | A1 | 9/2003 | Kopelman et al. |
| 2005/0069188 | A1 | 3/2005 | Rubbert et al. |
| 2009/0220134 | A1* | 9/2009 | Cahill ...................... G06T 7/30 382/128 |
| 2010/0166280 | A1* | 7/2010 | Endo ..................... G06T 11/00 382/131 |
| 2013/0218530 | A1* | 8/2013 | Deichmann .......... A61C 9/0046 703/1 |
| 2014/0293016 | A1* | 10/2014 | Benhimane ............. G06T 7/246 348/50 |
| 2015/0229840 | A1* | 8/2015 | Sawai ....................... G06T 7/33 348/36 |
| 2015/0235378 | A1* | 8/2015 | Rhee ..................... G06T 19/006 382/164 |
| 2015/0317821 | A1* | 11/2015 | Ding ......................... G06T 7/60 345/420 |
| 2015/0363971 | A1* | 12/2015 | Pan ......................... G06T 7/593 345/420 |
| 2016/0256035 | A1* | 9/2016 | Kopelman ......... A61B 1/00045 |
| 2016/0292533 | A1* | 10/2016 | Uchiyama ................ G06T 7/55 |
| 2016/0331463 | A1 | 11/2016 | Nötzli et al. |
| 2017/0372527 | A1* | 12/2017 | Murali ................. H04N 13/239 |
| 2018/0028065 | A1* | 2/2018 | Elbaz ................... A61B 5/7435 |
| 2018/0330471 | A1* | 11/2018 | Qin ............................ G06T 5/50 |
| 2020/0043186 | A1* | 2/2020 | Selviah ..................... G06T 7/33 |
| 2020/0232800 | A1* | 7/2020 | Bai ..................... G01C 21/3848 |
| 2021/0097703 | A1* | 4/2021 | Chang ....................... G06T 7/33 |

FOREIGN PATENT DOCUMENTS

| | | |
|---|---|---|
| JP | 2013-236750 A | 11/2013 |
| KR | 10-2013-0019676 A | 2/2013 |
| KR | 10-1730696 B1 | 4/2017 |
| KR | 10-2018-0088061 A | 8/2018 |
| KR | 10-1984028 B1 | 6/2019 |
| KR | 10-2019-0101694 A | 9/2019 |

OTHER PUBLICATIONS

Korean Notice of Allowance for Korean Application No. 10-2020-0065388 dated Jun. 21, 2022, 8 pages.
International Search Report for PCT/KR2021/006694 dated Sep. 1, 2021.
Extended European Search Report issued May 29, 2024 in Application No. 21814563.9.

* cited by examiner

THREE-DIMENSIONAL DATA ACQUISITION METHOD AND DEVICE, AND COMPUTER-READABLE STORAGE MEDIUM STORING PROGRAM FOR PERFORMING SAME METHOD

CROSS REFERENCE TO RELATED APPLICATIONS

This application is a National Stage of International Application No. PCT/KR2021/006694 filed May 28, 2021, claiming priority based on Korean Patent Application No. 10-2020-0065388 filed May 29, 2020.

TECHNICAL FIELD

The disclosure relates to a method and a device for obtaining three-dimensional data, and more particularly, to a method and a device for obtaining three-dimensional data with respect to a tooth by using an optical three-dimensional scanner.

BACKGROUND ART

A dental computer aided design (CAD)/computer aided manufacturing (CAM) technique is widely used for dental treatment, in particular, treatment such as prosthetic dentistry, etc. The most important issue in dental treatment using CAD/CAM is obtaining complex three-dimensional data with respect to the shape of an object, such as a tooth, a gum, a jawbone, etc. of a patient. In performing dental treatment, accurate calculation by a computer is possible when using the three-dimensional data obtained from the object.

For example, in order to obtain the three-dimensional data of the object in a process of dental CAD/CAM treatment, computed tomography (CT), magnetic resonance imaging (MRI), optical scanning, etc. may be used.

Formats and features of the obtained three-dimensional data may vary with a device or a method used for obtaining the three-dimensional data. Generally, the three-dimensional data may be classified into volumetric data and surface data according to a representation format.

The volumetric data may be obtained by X-ray CT, such as cone beam computed tomography (CBCT), or MRI, and may be represented in a format having an intensity value in a voxel structure.

In the dental CAD/CAM fields, an optical three-dimensional scanner is frequency used, in addition to CT. The optical three-dimensional scanner may obtain three-dimensional surface shape information about an object, for example, three-dimensional data of an impression material of a tooth, a plastic model obtained with respect to the impression material, or a tooth surface. The surface data may be recorded in a polygon mesh format and may include position information about apexes of a surface of an object and connection relationship information between the apexes.

DESCRIPTION OF EMBODIMENTS

Technical Problem

In order to obtain a good result of dental treatment using computer aided design (CAD)/computer aided manufacturing (CAM), three-dimensional data accurately reflecting a shape of an object is required.

Disclosed embodiments are to provide a method and a device for obtaining three-dimensional data accurately reflecting a shape of an object without distortion of a curvature of a dental arch, and a computer-readable storage medium having stored thereon a program for executing the method.

According to general optical scanning, a process of scanning the entire object is required, even when three-dimensional data with respect to only one or more regions included in the object is needed. For example, in order to obtain three-dimensional data with respect to molars at both sides, for prosthetic dentistry for the molars at both sides of lower jaws, it is needed to scan all of the teeth in the lower jaws from the molar at one side to the molar at the other side by using the optical three-dimensional scanner.

Disclosed embodiments are to provide a method and a device for obtaining three-dimensional data with respect to discontinuous regions of an object, and a computer-readable storage medium having stored thereon a program for executing the method.

Solution to Problem

According to an aspect of the disclosure, a method of obtaining three-dimensional data includes: obtaining three-dimensional reference data with respect to an object; aligning, on the three-dimensional reference data, a first frame obtained by scanning a first region of the object; aligning, on the three-dimensional reference data, a second frame obtained by scanning a second region of the object, at least a portion of the second region overlapping the first region; and obtaining the three-dimensional data by merging the first frame with the second frame based on an overlapping portion between the first region and the second region. Also, according to an embodiment of the disclosure, the aligning of the first frame on the three-dimensional reference data may include: selecting a first point on the three-dimensional reference data; obtaining the first frame by scanning the first region corresponding to the first point; and aligning the first frame on the three-dimensional reference data based on the first point.

Advantageous Effects of Disclosure

According to a method of obtaining three-dimensional data according to disclosed embodiments, three-dimensional data accurately reflecting a shape of an object may be obtained by aligning frames scanned in real time based on pre-obtained three-dimensional reference data.

According to a method of obtaining three-dimensional data according to disclosed embodiments, three-dimensional data including information with respect to one or more portions of an object by aligning frames scanned in real time based on pre-obtained three-dimensional reference data may be obtained.

BRIEF DESCRIPTION OF DRAWINGS

The disclosure may be easily understood based on the combination of the following detailed descriptions and the accompanying drawings, and reference numerals indicate structural elements.

BEST MODE

Figure 1A:
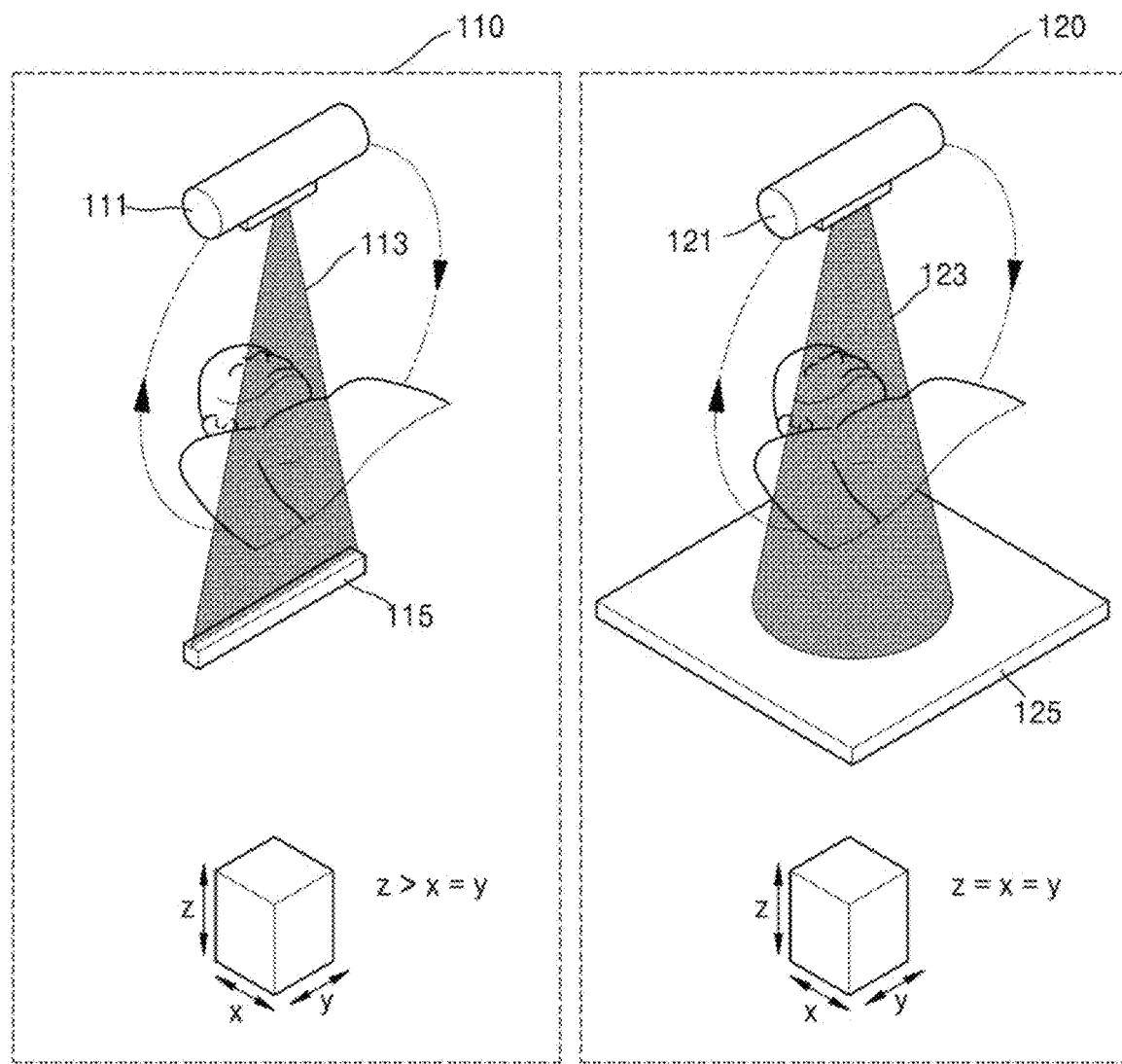
FIG. 1A is a diagram for describing a method, performed by a computed tomography (CT) scanner, of obtaining volumetric data, according to an embodiment.

According to an aspect of the disclosure, a method of obtaining three-dimensional data includes: obtaining three-dimensional reference data with respect to an object; aligning, on the three-dimensional reference data, a first frame obtained by scanning a first region of the object; aligning, on the three-dimensional reference data, a second frame obtained by scanning a second region of the object, at least a portion of the second region overlapping the first region; and obtaining the three-dimensional data by merging the first frame with the second frame based on an overlapping portion between the first region and the second region. Also, according to an embodiment of the disclosure, the aligning of the first frame on the three-dimensional reference data may include: selecting a first point on the three-dimensional reference data; obtaining the first frame by scanning the first region corresponding to the first point; and aligning the first frame on the three-dimensional reference data based on the first point.

Also, according to an embodiment of the disclosure, the aligning of the second frame on the three-dimensional reference data may include aligning the second frame on the three-dimensional reference data based on a three-dimensional coordinate value of the aligned first frame. Also, according to an embodiment of the disclosure, the aligning of the second frame on the three-dimensional reference data may include aligning the second frame on the three-dimensional reference data based on the first point and a three-dimensional coordinate value of the aligned first frame.

Also, according to an embodiment of the disclosure, the method may further include: selecting a second point on the three-dimensional reference data; aligning, on the three-dimensional reference data, a third frame obtained by scanning a third region of the object corresponding to the second point; aligning, on the three-dimensional reference data, a fourth frame obtained by scanning a fourth region of the object, at least a portion of the fourth region overlapping the third region; and obtaining the three-dimensional data by merging the third frame with the fourth frame based on an overlapping portion between the third region and the fourth region.

Also, according to an embodiment of the disclosure, the three-dimensional reference data may be surface data of the object extracted from volumetric data obtained by computed tomography (CT) or magnetic resonance imaging (MRI).

Also, according to an embodiment of the disclosure, the method may further include displaying the three-dimensional data on an object image generated from the three-dimensional reference data.

Also, according to an embodiment of the disclosure, the selecting of the first point on the three-dimensional reference data may include selecting the first point on the three-dimensional reference data based on a user input.

Also, according to an embodiment of the disclosure, the selecting of the first point on the three-dimensional reference data may include automatically selecting the first point on the three-dimensional reference data according to a predetermined reference.

Also, according to an embodiment of the disclosure, the method may further include: performing first segmentation on volumetric data obtained by CT or MRI to obtain the three-dimensional reference data; and identifying a region corresponding to a plurality of teeth included in the object by performing second segmentation on the three-dimensional reference data.

Also, according to an embodiment of the disclosure, the selecting of the first point on the three-dimensional reference data may further include selecting a point corresponding to one tooth from among a plurality of teeth included in the object as the first point on the three-dimensional reference data.

Also, according to an embodiment of the disclosure, the first frame or the second frame may be obtained by an optical three-dimensional scanner and may include shape information about a surface of the object.

Also, according to an embodiment of the disclosure, the aligning of the first frame on the three-dimensional reference data may include: extracting a plurality of apexes on the three-dimensional reference data based on the first point; extracting, from the first frame, a plurality of corresponding points respectively corresponding to the plurality of apexes; and aligning the first frame on the three-dimensional reference data, based on a difference of distance values between the plurality of apexes and the plurality of corresponding points.

According to another aspect of the disclosure, a device for obtaining three-dimensional data includes: a display; a communication interface configured to communicate with an optical three-dimensional scanner; and at least one processor configured to control the three-dimensional data by executing at least one instruction, wherein the at least one processor is configured to: obtain three-dimensional reference data with respect to an object; obtain a first frame by scanning a first region of the object via the optical three-dimensional scanner and align the obtained first frame on the three-dimensional reference data; obtain a second frame by scanning a second region of the object, at least a portion of the second region overlapping the first region, and align the obtained second frame on the three-dimensional reference data; and obtain the three-dimensional data by merging the first frame with the second frame based on an overlapping portion between the first region and the second region.

According to another aspect of the disclosure, a computer-readable recording medium has stored thereon a program for executing the method of obtaining the three-dimensional data.

MODE OF DISCLOSURE

In the present specification, principles of the disclosure are described and embodiments are disclosed to clearly convey the scope of the claims of the disclosure and for one of ordinary skill in the art to implement the disclosure. The disclosed embodiments may be implemented in various forms.

Throughout the specification, like reference numerals refer to like elements. Not all elements of the embodiments are described in this specification, and general aspects in the art or the same aspects of the embodiments are not described. The term "part" or "portion" used in the specification may be implemented as software or hardware, and according to embodiments, a plurality of "units" may be implemented as one unit (element), or one "unit" may include a plurality of units (elements). Hereinafter, by referring to the accompanying drawings, the operating principles and the embodiments of the disclosure are described.

In this disclosure, an "object" refers to an object that is to be captured and may include a human being, an animal, or a part thereof. For example, an object may include a part of a human body (organs, viscera, or the like), an artificial structure which may be coupled to or inserted into an object, a phantom, or the like. Hereinafter, for example, a case of obtaining three-dimensional data with respect to an oral cavity including at least one tooth as an object is described. For example, an object may include a tooth, a gum, at least a portion of an oral cavity, and/or an artificial structure (for example, an orthodontic appliance including a bracket and a wire, an implant, an artificial tooth, an orthodontic auxiliary instrument inserted into the oral cavity, etc.) which may be inserted into the oral cavity. However, the disclosure is not limited to the case of obtaining the three-dimensional data with respect to the oral cavity and may be applied to cases of obtaining three-dimensional data with respect to various objects.

In this disclosure, an "image" may include a medical image obtained by a medical imaging device, such as a magnetic resonance imaging (MIR) device, a computed tomography (CT) device, an ultrasonic imaging device, an X-ray imaging device, an optical three-dimensional imaging device, etc.

Also, in this disclosure, an "image" may include a two-dimensional image with respect to an object, or a three-dimensional model or a three-dimensional image three-dimensionally representing an object. For example, in this disclosure, an image may include a three-dimensional image generated by rendering volumetric data obtained by CT or MRI or surface data extracted from the corresponding volumetric data.

In this disclosure, an image may include both of a two-dimensional frame and a three-dimensional frame. For example, the image may include a three-dimensional frame represented in a point cloud format or a polygon mesh format.

Also, in this disclosure, an image may denote data needed to represent an object two-dimensionally or three-dimensionally, for example, raw data obtained from at least one image sensor. In detail, the raw data may be a two-dimensional (2D) image obtained to generate three-dimensional data with respect to an object. The raw data may be obtained by at least one image sensor included in an optical three-dimensional scanner, when an object is scanned by using the optical three-dimensional scanner (for example, an intraoral cavity scanner).

Hereinafter, embodiments are described in detail with reference to the drawings.

A dental computer aided design (CAD)/computer aided manufacturing (CAM) technique is widely used for dental treatment, in particular, treatment, such as prosthetic dentistry, etc. For example, in order to obtain three-dimensional data of an object in a process of dental CAD/CAM treatment, CT, MRI, optical scanning, etc. may be used. In general, the three-dimensional data may be classified into volumetric data and surface data according to a representation format.

FIG. 1A is a diagram for describing a method, performed by a CT scanner, of obtaining volumetric data, according to an embodiment.

CT is a diagnosis method that projects X-rays or ultrasonic waves to a human body from various angles by using a CT scanner and refigures a result of projection via a computer to process a shape of an internal section of the human body as an image.

As illustrated in FIG. 1A, a general CT scanner 110 may irradiate an X-ray beam 113 having a fan shape from an X-ray source 111, may measure a degree of transmittance of the X-ray beam 113 with respect to an object by using a detector 115, and may reconfigure a measured result to obtain three-dimensional data. However, a cone beam computed tomography (CBCT) scanner 120 may use an X-ray beam 123 having a cone shape. The CBCT scanner 120 may irradiate the X-ray beam 123 having the cone shape from an X-ray source 121, may measure a degree of transmittance of the X-ray beam 123 with respect to an object by using a detector 125, and may reconfigure a measured result to obtain three-dimensional data. Compared to the general CT scanner 110, the CBCT scanner 120 may have a less amount of radiation exposure, and thus, the CBCT scanner 120 is widely used in the fields of dental treatment. The three-dimensional data obtained by the CBCT scanner 120 may be represented in the format of volumetric data including a plurality of voxels having an intensity value.

Figure 1B:
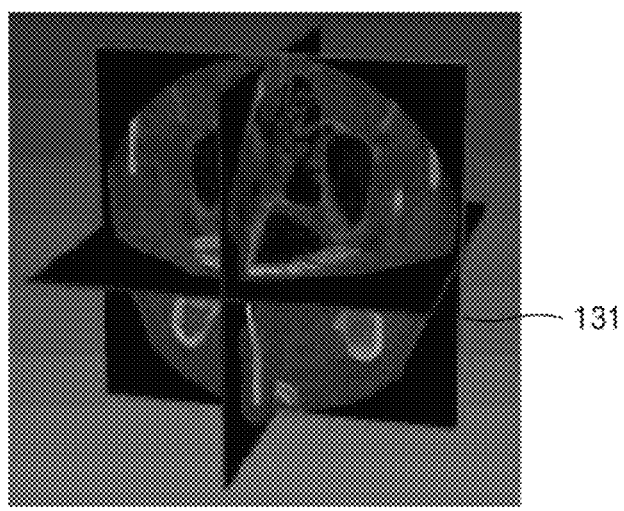
FIG. 1B illustrates an example of surface data extracted by segmentation on volumetric data, according to an embodiment.
Figure 1B:
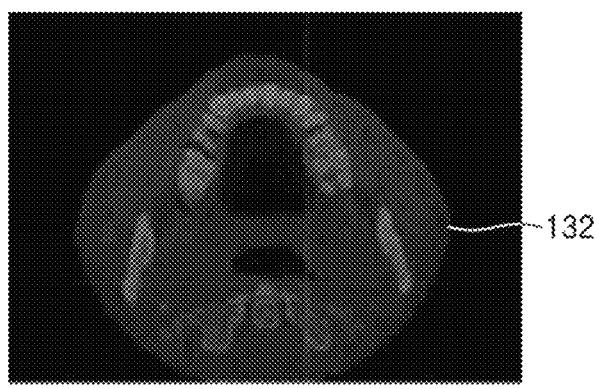
Figure 1B:
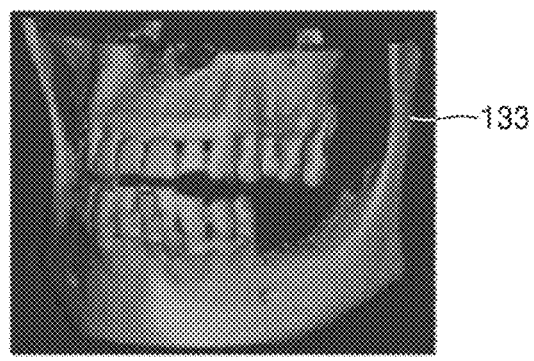

FIG. 1B illustrates an example of surface data extracted by segmentation on volumetric data, according to an embodiment.

An image 131 of FIG. 1B is an example of volumetric data obtained by CT. The volumetric data obtained by CT may have varying intensities according to a property of an organ. Therefore, segmentation is performed to segment intensity information about the CT volumetric data based on a predetermined threshold value, in order to extract information about a surface of an object from the CT volumetric data.

According to an embodiment, the threshold value for the segmentation may be configured based on a user input.

For example, a user interface (UI) of software for medical image processing may provide a function of adjusting the threshold value. As indicated in an image 132 of FIG. 1B, a user may adjust the threshold value through the UI and identify surface data generated based on the threshold value. Different forms of surface data may be generated according to the threshold value input by the user, and the user may identify the surface data with the naked eye and configure a threshold value which is deemed to be appropriate. The surface data may be ultimately extracted from the volumetric data based on the configured threshold value.

An image 133 of FIG. 1B shows an example of the surface data generated from the volumetric data through the segmentation process.

Here, the surface data generated through the segmentation on the volumetric data may vary according a value of the configured threshold value. For example, the surface data extracted from the CT volumetric data with respect to a head of a human being may be data with respect to a surface of a skull or data with respect to a skin of the human being according to the threshold value configured by the user.

In addition to the method of using the threshold value, active contour methods, such as region growing, level-set, etc., may be used for segmentation.

In the dental CAD/CAM fields, an optical three-dimensional scanner is frequency used, in addition to CT. The optical three-dimensional scanner may obtain three-dimensional surface shape information from an object. For example, the optical three-dimensional scanner may obtain three-dimensional data of an impression material of a tooth, a plastic model obtained with respect to the impression material, or a surface of the tooth. The three-dimensional data with respect to a surface of an object may be represented in a polygon mesh format including position information about apexes of the surface of the object and connection relationship information about the apexes.

Figure 2:
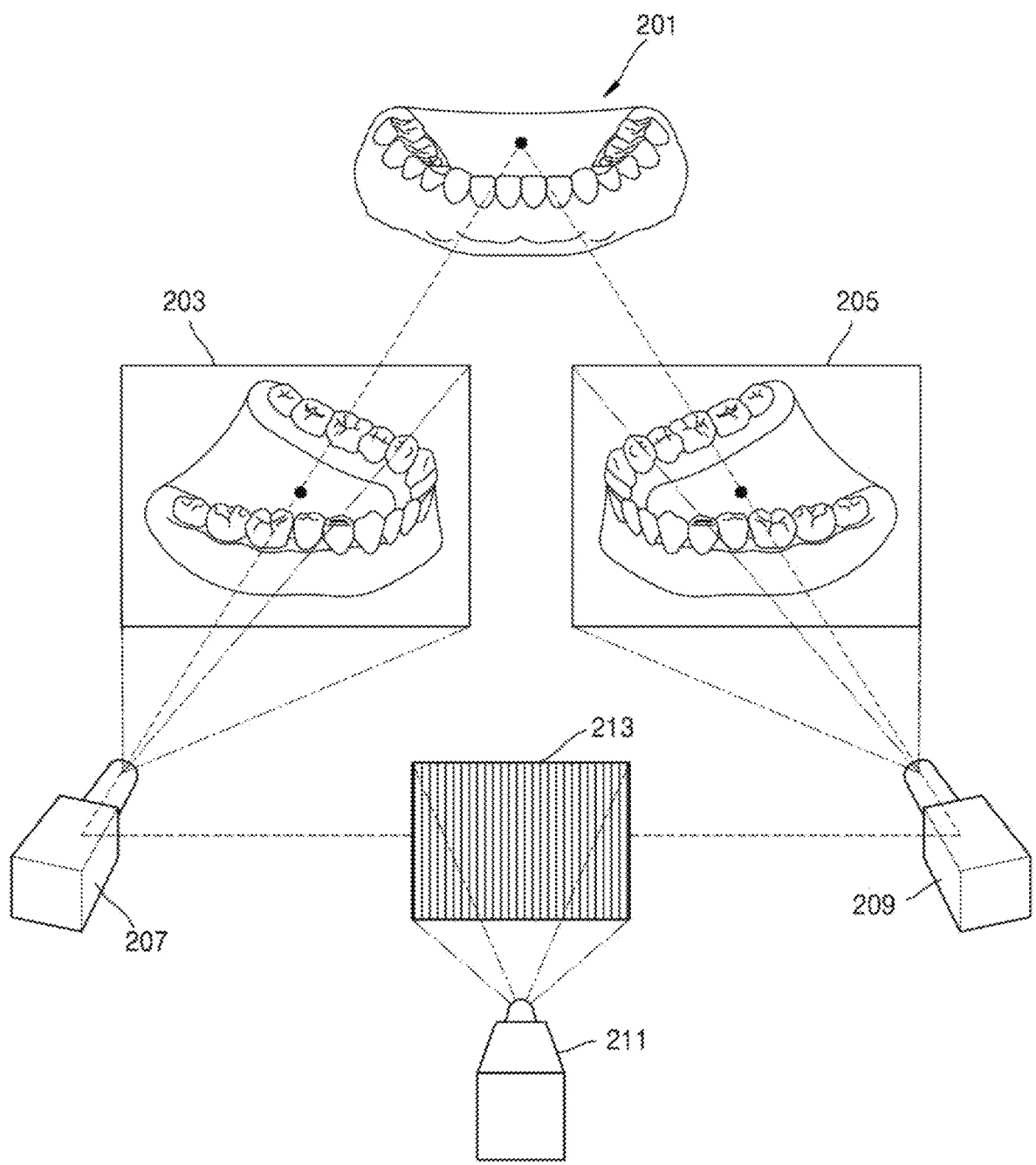
FIG. 2 is a diagram for describing a method, performed by an optical three-dimensional scanner, of obtaining surface data, according to an embodiment.

FIG. 2 is a diagram for describing a method, performed by an optical three-dimensional scanner, of obtaining surface data, according to an embodiment.

According to an embodiment, in order to obtain three-dimensional data with respect to a surface of an object by using the optical three-dimensional scanner, a structured light with stereo vision method may be used.

The optical three-dimensional scanner according to an embodiment may include at least two cameras 207 and 209 and one projector 211 capable of projecting structured light 213. The optical three-dimensional scanner according to an embodiment may project the structured light 213 to an object 201 and may obtain L image data 203 corresponding to a left field of view and R image data 205 corresponding to a right field of view by using an L camera 207 corresponding to the left field of view and an R camera 209 corresponding to the right field of view, respectively. The L image data 203 and the R image data 205 may be reconfigured as a three-dimensional frame indicating the surface of the object.

The optical three-dimensional scanner may scan the object by a predetermined time interval (for example, 10 to 30 frames per second) while moving around the object and obtain a plurality of three-dimensional frames and may merge or align the plurality of three-dimensional frames to reconfigure three-dimensional data with respect to the entire object.

Figure 3:
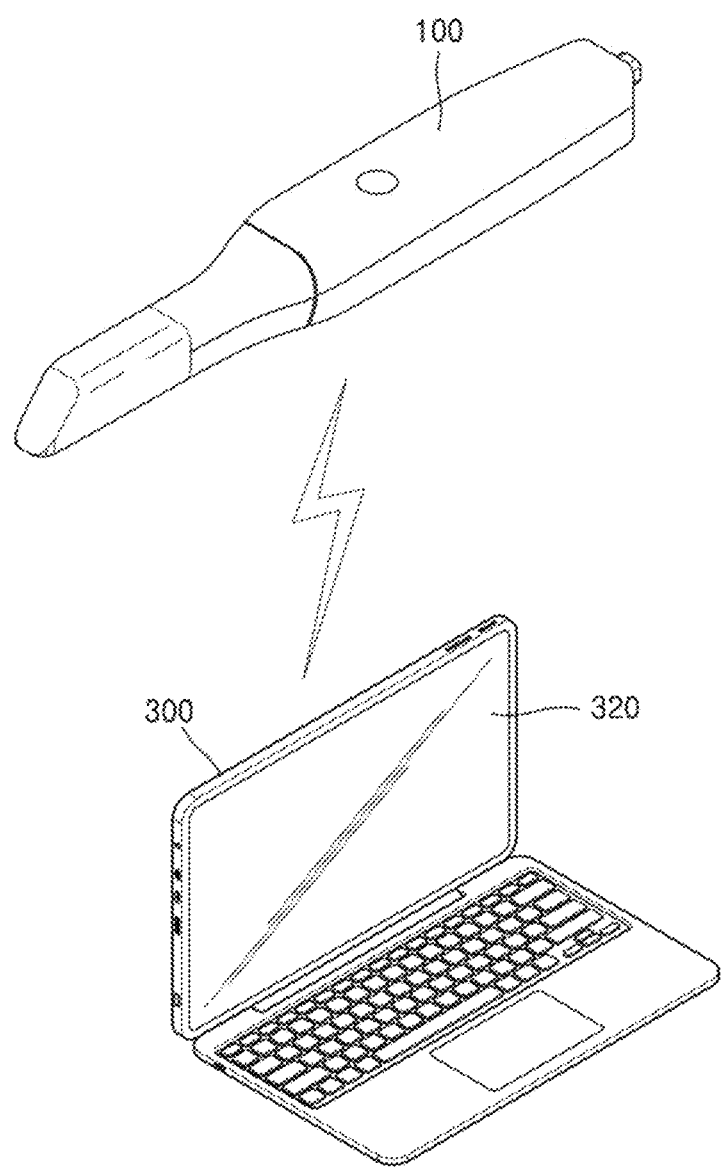
FIG. 3 is a diagram for describing a three-dimensional data obtaining system, according to an embodiment.

FIG. 3 is a diagram for describing a three-dimensional data obtaining system, according to an embodiment.

As illustrated in FIG. 3, the three-dimensional data obtaining system according to an embodiment of the disclosure may include an optical three-dimensional scanner 100 and a three-dimensional data obtaining device 300.

The optical three-dimensional scanner 100 according to an embodiment may transmit, to the three-dimensional data obtaining device 300, raw data including L image data and R image data obtained from an object according to the structured light with stereo vision method. The three-dimensional data obtaining device 300 may generate, based on the transmitted raw data, three-dimensional data that three-dimensionally represents a shape of a surface of the object. The optical three-dimensional scanner 100 according to another embodiment may generate a three-dimensional frame by reconfiguring the raw data including the L image data and the R image data obtained from the object and may transmit the generated three-dimensional frame to the three-dimensional data obtaining device 300.

The optical three-dimensional scanner 100 according to an embodiment may include a medical device for obtaining an image of an oral cavity. In detail, the optical three-dimensional scanner 100 may be a device for generating a three-dimensional model with respect to the oral cavity including at least one tooth by scanning the tooth in a non-contact way by being inserted into the oral cavity. Also, the optical three-dimensional scanner 100 may have a shape which may be inserted into and withdrawn from the oral cavity and may scan an internal state of the oral cavity of a patient by using at least one image sensor (for example, an optical camera, etc.).

In order to image a surface of an object, that is, at least one from among a tooth in the oral cavity, a gum, and an artificial structure (e.g., an orthodontic device including a bracket and a wire, an implant, an artificial tooth, an orthodontic auxiliary instrument inserted into the oral cavity, etc.), the optical three-dimensional scanner 100 may obtain surface information with respect to the object as raw data, and based on the obtained raw data, may perform three-dimensional calculation, such as merging, etc., and display a result on a display.

The raw data obtained by the optical three-dimensional scanner 100 or a three-dimensional frame obtained based on the raw data may be transmitted to the three-dimensional data obtaining device 300 connected to the optical three-dimensional scanner 100 through a wired or wireless communication network.

The three-dimensional data obtaining device 300 according to an embodiment may be connected to the optical three-dimensional scanner 100 through the wired or wireless communication network and may receive, from the optical three-dimensional scanner 100, the raw data obtained by scanning the object or the three-dimensional frame.

The three-dimensional data obtaining device 300 may include all of electronic devices which may generate, process, display, and/or transmit three-dimensional data or a three-dimensional image with respect to the object, based on the received raw data or three-dimensional frame. For example, the three-dimensional data obtaining device 300 may include a computing device, such as a smartphone, a laptop computer, a desk top computer, a personal digital assistant (PDA), a tablet personal computer (PC), etc., but is not limited thereto.

The three-dimensional data obtaining device 300 may generate at least one of information required for diagnosing the object and an object image, based on the data received from the optical three-dimensional scanner 100, and may display the generated information and/or image through a display 320.

The three-dimensional data obtaining device 300 according to an embodiment may analyze three-dimensional data or a three-dimensional image with respect to the object and may process, display, and/or transmit an analyzed result.

Also, the three-dimensional data obtaining device 300 according to an embodiment may store and execute exclusive software synchronized to the optical three-dimensional scanner 100. Here, the exclusive software may be referred to as an exclusive program or an exclusive application. When the three-dimensional data obtaining device 300 operates in synchronization with the optical three-dimensional scanner 100, the exclusive software stored in the three-dimensional data obtaining device 300 may be connected to the optical three-dimensional scanner 100 and may receive data obtained by scanning the object, in real time. For example, there may be exclusive software for processing data obtained through oral cavity scanning, with respect to i500 corresponding to the i500 product, an oral cavity scanner of the present applicant. The three-dimensional data obtaining device 300 may store and execute the exclusive software corresponding to the i500 product. The exclusive software may perform at least one of operations of obtaining, processing, storing, and/or transmitting an oral image.

The exclusive software may be stored in a processor or a memory of the three-dimensional data obtaining device 300. Also, the exclusive software may provide a UI for using data obtained by the optical three-dimensional scanner. A screen of the UI provided by the exclusive software may include a three-dimensional image with respect to an object generated according to a disclosed embodiment. For example, according to a disclosed embodiment, the UI screen provided by the exclusive software may be any one of UI screens illustrated in FIGS. 5A to 8B.

According to various embodiments of the disclosure, a detailed method, performed by the three-dimensional data obtaining device 300, of obtaining three-dimensional data with respect to an object, is described in detail below with reference to FIGS. 4A to 10.

Figure 4A:
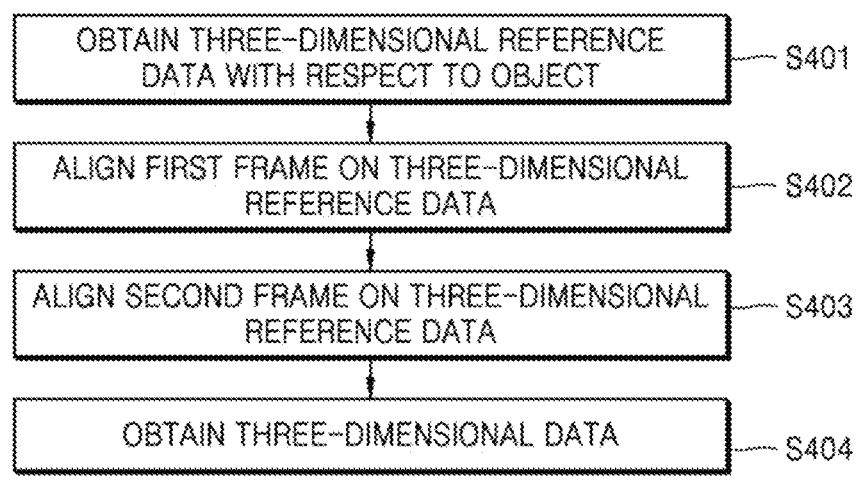
FIG. 4A is a flowchart of a method, performed by a three-dimensional data obtaining device, of obtaining three-dimensional data, according to an embodiment.

FIG. 4A is a flowchart of a method, performed by a three-dimensional data obtaining device, of obtaining three-dimensional data, according to an embodiment.

In operation S401, the three-dimensional data obtaining device 300 according to an embodiment of the disclosure may obtain three-dimensional reference data with respect to an object. The three-dimensional reference data according to an embodiment may be volumetric data obtained by CT or MRI or may be surface data of the object extracted from the volumetric data obtained by CT or MRI.

For example, the three-dimensional data obtaining device 300 may obtain the three-dimensional reference data from an embedded memory, an external server, or an external device (for example, a medical image capturing device).

As another example, the three-dimensional data obtaining device 300 may obtain the volumetric data obtained by CT or MRI, from the embedded memory, the external server, or the external device, and may directly extract the three-dimensional reference data from the obtained volumetric data.

The three-dimensional data obtaining device 300 according to an embodiment may perform segmentation to extract, from the volumetric data, the three-dimensional reference data, which is information about a surface of an object. For example, the three-dimensional data obtaining device 300 may perform segmentation to segment intensity information about the volumetric data based on a predetermined threshold value, and thus, may have a dental organ distinguished from other organs.

For example, the threshold value for the segmentation may be configured based on a user input. The three-dimensional data obtaining device 300 may provide a UI through which a user may adjust the threshold value for the segmentation. The three-dimensional data obtaining device 300 may display the surface data generated based on the configured threshold value to the user. The user may select a threshold value which is deemed to be the most appropriate, based on the surface data generated in different forms according to the threshold value.

As another example, the threshold value for the segmentation may be automatically configured by the three-dimensional data obtaining device 300. The three-dimensional data obtaining device 300 may determine the threshold value by taking into a result of analyzing the volumetric data and/or various types of data. The three-dimensional data obtaining device 300 may determine the threshold value based on at least one of the result of analyzing the volumetric data, data previously trained in relation to the segmentation, a user's past segmentation record, a user configuration, or information about which part of a human body an object is.

A segmentation method according to various embodiments of the disclosure is not limited to the method using the threshold value described above, and active contour methods, such as region growing, level set, etc., may be used.

The three-dimensional data obtaining device 300 according to an embodiment may obtain the information about the surface of the object from the volumetric data by performing various segmentation operations. The three-dimensional data obtaining device 300 according to an embodiment may obtain the three-dimensional reference data including the information about the surface of the object by performing first segmentation on the volumetric data and may identify regions corresponding to a plurality of teeth included in the object by performing second segmentation on the three-dimensional reference data.

The three-dimensional data obtaining device 300 according to an embodiment may generate an object image from the three-dimensional reference data and display the object image.

Figure 5A:
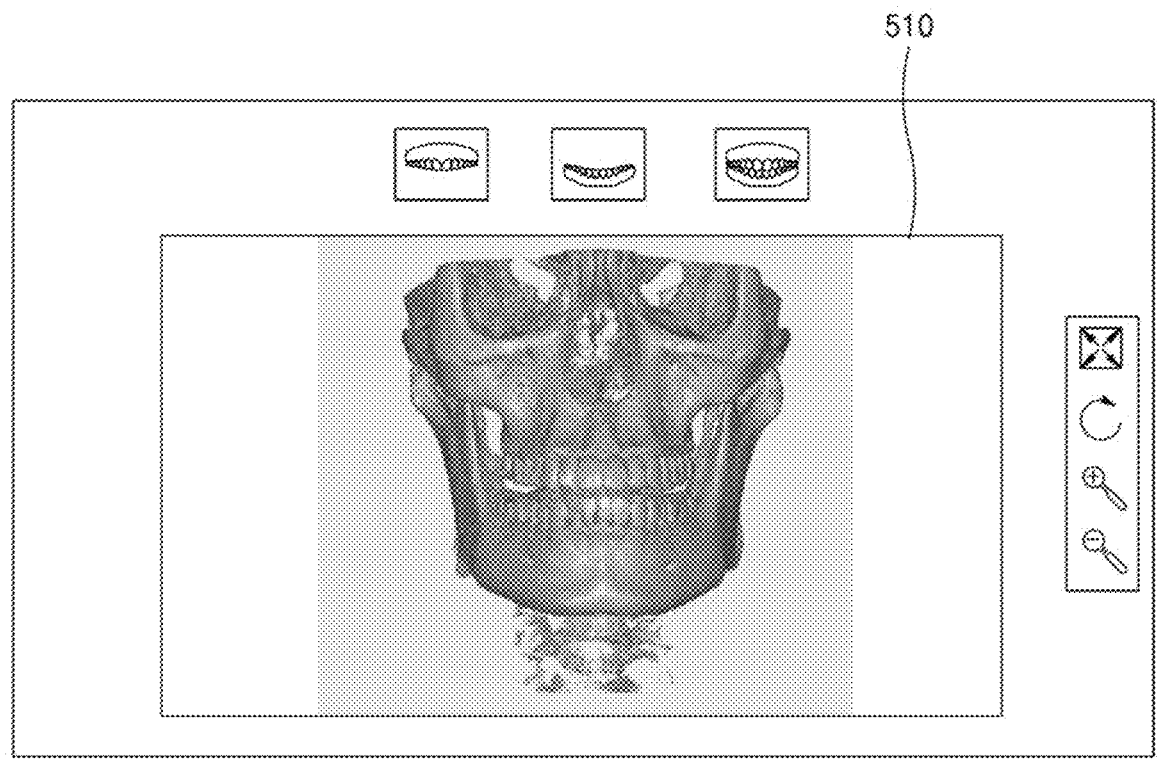
FIG. 5A illustrates an example of an object image displayed by a three-dimensional data obtaining device, according to an embodiment.

FIG. 5A illustrates an example of a screen on which the three-dimensional data obtaining device 300 displays an object image 510 generated from the three-dimensional reference data, according to an embodiment.

When the segmentation on the volumetric data is appropriately performed, the three-dimensional reference data including information about a surface of the skull may be obtained. The three-dimensional data obtaining device 300 according to an embodiment may display the object image 510 generated from the three-dimensional reference data including the information about the surface of the skull, as illustrated in FIG. 5A. For example, the object image may be represented to be semi-transparent or in a gray scale.

The object image generated from the three-dimensional reference data is not limited to the example illustrated in FIG. 5A.

Figure 5B:
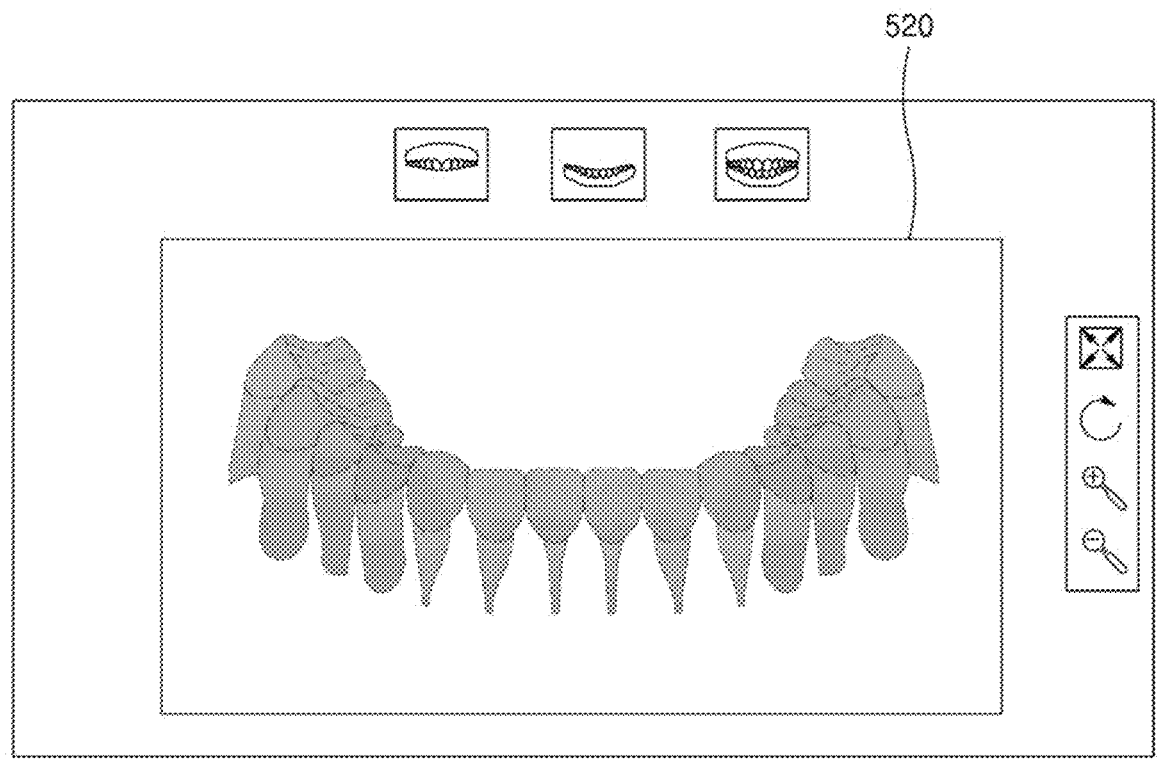
FIG. 5B illustrates an example of an object image displayed by a three-dimensional data obtaining device, according to an embodiment.

FIG. 5B illustrates an example of a screen on which the three-dimensional data obtaining device 300 displays an object image 520 generated from the three-dimensional reference data, according to an embodiment.

The three-dimensional data obtaining device 300 according to an embodiment may obtain the three-dimensional reference data including information about a surface of a plurality of teeth in lower jaws. The three-dimensional data obtaining device 300 according to an embodiment may display the object image 520 generated from the three-dimensional reference data including the information about the surface of the plurality of teeth, as illustrated in FIG. 5B. However, the displaying of the object image generated from the three-dimensional reference data, via the three-dimensional data obtaining device 300, is not an essential operation. The three-dimensional data obtaining device 300 according to an embodiment may omit the operation of displaying the object image and may perform subsequent operation S402.

In operation S402, the three-dimensional data obtaining device 300 according to an embodiment of the disclosure may align a first frame obtained by scanning a first region of the object on the three-dimensional reference data.

The three-dimensional data obtaining device 300 according to an embodiment may obtain the first frame including shape information about the surface of the object via an optical three-dimensional scanner. For example, the three-dimensional data obtaining device 300 may obtain, in a wired or wireless manner, raw data from the optical three-dimensional scanner using a structured light with stereo vision method, and may reconfigure the raw data into the first frame according to an optical triangulation method. With respect to a detailed method, performed by the three-dimensional data obtaining device 300, of obtaining the scan data of the object, according to an embodiment, the descriptions of FIGS. 2 and 3 may be applied.

The three-dimensional data obtaining device 300 according to an embodiment may align the first frame on the three-dimensional reference data.

The three-dimensional data obtaining device 300 according to an embodiment may use various algorithms for aligning the three-dimensional reference data with the first frame. For example, an iterative closest point (ICP) algorithm may be used.

ICP is a method of aligning two different pieces of three-dimensional data by minimizing a distance deviation. The three-dimensional data obtaining device 300 may perform the aligning operation by using the ICP algorithm through the following processes.

First, the three-dimensional data obtaining device 300 may extract (a first operation) apexes to be used for calculation, from among apexes of the three-dimensional reference data. The operation of extracting the apexes to be used for calculation may be referred to as sampling. The three-dimensional data obtaining device 300 according to an embodiment may extract the plurality of apexes of the three-dimensional reference data based on an initial position. The three-dimensional data obtaining device 300 may determine (a second operation), from the first frame, corresponding points corresponding to the extracted apexes. The three-dimensional data obtaining device 300 may align the first frame on the three-dimensional reference data based on a difference of distance values between the plurality of apexes and the plurality of corresponding points.

The three-dimensional data obtaining device 300 according to an embodiment may derive (a third operation) an objective function having a distance between the extracted apexes and a group of the determined corresponding points, as an energy, and may calculate (a fourth operation) a shift function between the three-dimensional reference data and the first frame, for minimizing a value of the objective function. The three-dimensional data obtaining device 300 may align (a fifth operation) the first frame on the three-dimensional reference data based on the calculated shift function and may repeatedly perform the first to fifth operations described above until a completion condition is met to increase the accuracy of position alignment.

The three-dimensional data obtaining device 300 according to an embodiment may determine the initial position for aligning the first frame on the three-dimensional reference data. For example, the three-dimensional reference data obtaining device 300 may determine a first point on the three-dimensional reference data as the initial position, based on a user input. As another example, the three-dimensional reference data obtaining device 300 may automatically determine the first point on the three-dimensional reference data as the initial position according to a predetermined reference. The three-dimensional data obtaining device 300 may determine the first point corresponding to one tooth from among a plurality of teeth included in the object as the initial position. The three-dimensional data obtaining device 300 may align the first frame on the three-dimensional reference data based on the determined initial position.

In operation S403, the three-dimensional data obtaining device 300 according to an embodiment of the disclosure may align, on the three-dimensional reference data, a second frame obtained by scanning a second region of the object, the second region having at least a portion overlapping the first region of the object.

The three-dimensional data obtaining device 300 according to an embodiment may obtain frames scanned by the optical three-dimensional scanner by a predetermined time interval, in real time. The first frame and the second frame may be obtained by the optical three-dimensional scanner moved by a user. The second frame may indicate the second region having at least a portion overlapping the first region of the object indicated by the first frame.

The three-dimensional data obtaining device 300 according to an embodiment may align the second frame on the three-dimensional reference data.

The three-dimensional data obtaining device 300 according to an embodiment may align the second frame on three-dimensional reference data based on a three-dimensional coordinate value of the first frame. The three-dimensional data obtaining device 300 may align the second frame on an optimum position by taking into account the three-dimensional reference data and the first frame aligned on the three-dimensional reference data.

The three-dimensional data obtaining device 300 according to an embodiment may obtain, from the optical scanner, frames obtained by scanning the object by a predetermined time interval, in real time. For example, the three-dimensional data obtaining device 300 may obtain the first frame from the optical scanner within a predetermined time from a time point at which the optical scanner scans the first frame and may obtain the second frame within a predetermined time from a time point at which the optical scanner scans the second frame. Thus, the three-dimensional data obtaining device 300 according to an embodiment may easily and quickly align the second frame obtained next to the first frame, after successfully aligning the first frame on the three-dimensional reference data. This may be because the first region of the object indicated by the first frame and the second region of the object indicated by the second frame scanned after a short time interval are three-dimensionally very close to each other.

For example, when the three-dimensional data obtaining device 300 aligns the frames on the three-dimensional reference data by using the ICP algorithm, the initial position used to align the first frame and the initial position used to align the second frame may be three-dimensionally very close to each other. Thus, the three-dimensional data obtaining device 300 may align the second frame on the three-dimensional reference data by taking into account the three-dimensional position of the first frame and/or the initial position used to align the first frame.

The three-dimensional coordinate value of the first frame may denote a coordinate value indicating a position of the first frame that is determined by three-dimensionally aligning the first frame on the three-dimensional reference data. Hereinafter, referring to FIG. 4B, a method, performed by the three-dimensional data obtaining device 300, of aligning the second frame on the three-dimensional reference data based on the three-dimensional coordinate value of the first frame, is described, according to an embodiment.

Figure 4B:
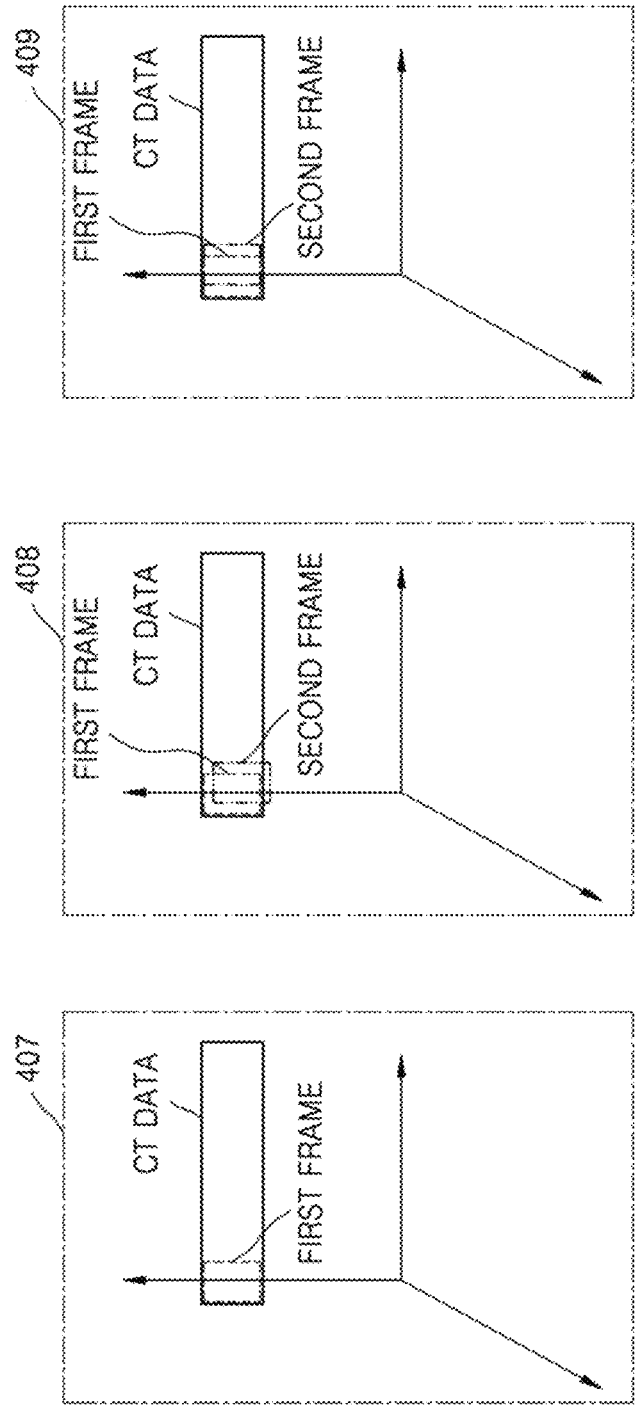
FIG. 4B is a diagram for describing a method, performed by a three-dimensional data obtaining device, of aligning a second frame on three-dimensional reference data based on a three-dimensional coordinate value of a first frame, according to an embodiment.

FIG. 4B is a diagram for describing a method, performed by a three-dimensional data obtaining device, of aligning a second frame on three-dimensional reference data based on a three-dimensional coordinate value of a first frame, according to an embodiment.

A diagram 407 of FIG. 4B illustrates the first frame aligned on CT data used as the three-dimensional reference data. The three-dimensional data obtaining device 300 may align the first frame on the CT data on a three-dimensional coordinate system of an x axis, a y axis, and a z axis and may obtain the three-dimensional coordinate value of the first frame.

Next, as illustrated in a diagram 408, when the three-dimensional data obtaining device 300 obtains the second frame within a predetermined time from a time point at which the first frame is obtained from the optical scanner, the three-dimensional data obtaining device 300 may estimate that a position to align the second frame is near the three-dimensional coordinate value of the first frame. This may be based on the assumption that the first region of the object indicated by the first frame and the second region of the object indicated by the second frame scanned in a very short time period after the first frame are three-dimensionally very close to each other.

Based on this assumption, the three-dimensional data obtaining device 300 may determine the initial position of the second frame based on the three-dimensional coordinate value of the first frame and may perform the ICP to finally align the second frame on the CT data, as illustrated in a diagram 409.

Referring to FIG. 4A again, in operation S404, the three-dimensional data obtaining device 300 according to an embodiment may obtain three-dimensional data by merging the first frame and the second frame based on an overlapping portion.

According to another embodiment of the disclosure, after determining an initial position on the three-dimensional reference data, a scanned frame may be aligned on the three-dimensional reference data based on the initial position.

Figure 4C:
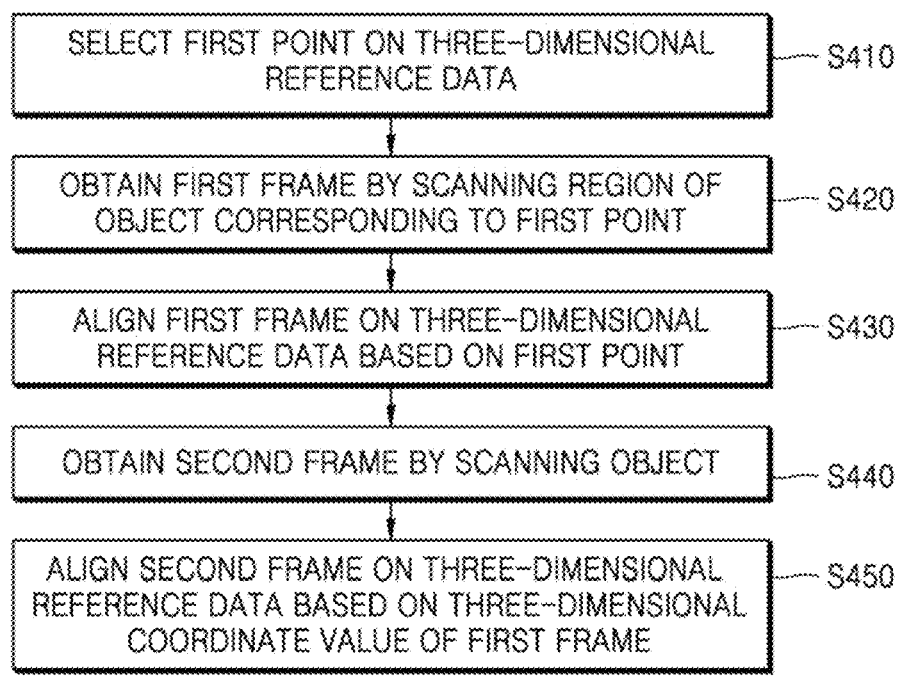
FIG. 4C is a flowchart of a method, performed by a three-dimensional data obtaining device, of obtaining three-dimensional data, according to an embodiment.

FIG. 4C is a flowchart of a method, performed by a three-dimensional data obtaining device, of obtaining three-dimensional data, according to an embodiment. Operations S402 and S403 of FIG. 4A may respectively correspond to operations S430 and S450 of FIG. 4C, and the descriptions about the operations of FIG. 4A may be applied to FIG. 4C, and thus, repeated descriptions are not given.

In operation S410, the three-dimensional data obtaining device 300 according to an embodiment of the disclosure may select a first point on three-dimensional reference data with respect to an object.

First, the three-dimensional data obtaining device 300 according to an embodiment may obtain the three-dimensional reference data with respect to the object. The three-dimensional reference data according to an embodiment may be surface data of the object, extracted from volumetric data obtained by CT or MRI.

For example, the three-dimensional data obtaining device 300 may obtain the three-dimensional reference data from an embedded memory, an external server, or an external device (for example, a medical image capturing device).

As another example, the three-dimensional data obtaining device 300 may obtain, from the embedded memory, the external server, or the external device, the volumetric data obtained by CT or MRI and may directly extract the three-dimensional reference data from the obtained volumetric data.

For example, the three-dimensional data obtaining device 300 may extract, from the volumetric data, the three-dimensional reference data including information about the surface of the object, by performing segmentation. Voxels of the volumetric data obtained by a CT scanner may have varying intensities according to a property of an organ. Thus, a dental organ and other organs may be distinguished from each other through the segmentation that segments, based on a predetermined threshold value, the intensity information about the volumetric data with respect to a head of a human being. Here, according to a value of the predetermined threshold value, an object indicated by the surface data generated as a result of the segmentation may vary. For example, the surface data extracted from the CT volumetric data obtained with respect to the head of the human being may be data indicating a surface of the skull or data indicating a surface of the scalp, according to the threshold value.

According to an embodiment, the threshold value for the segmentation may be configured based on a user input.

For example, the three-dimensional data obtaining device 300 may provide a UI through which a user may adjust the threshold value for the segmentation. The three-dimensional data obtaining device 300 may display the surface data generated based on the configured threshold value to the user. The user may select a threshold value which is deemed to be the most appropriate, based on different forms of the surface data generated based on the threshold value.

As another example, the threshold value for the segmentation may be automatically configured by the three-dimensional data obtaining device 300. The three-dimensional data obtaining device 300 may determine the threshold value by taking into a result of analyzing the volumetric data and/or various types of data. The three-dimensional data obtaining device 300 may determine the threshold value based on at least one of the result of analyzing the volumetric data, data previously trained in relation to the segmentation, a user's past segmentation record, a user configuration, or information about which part of a human body an object is.

A segmentation method according to various embodiments of the disclosure is not limited to the method using the threshold value described above, and active contour methods, such as region growing, level set, etc., may be used.

The three-dimensional data obtaining device 300 according to an embodiment may obtain the information about the surface of the object from the volumetric data by performing various segmentation operations. The three-dimensional data obtaining device 300 according to an embodiment may obtain the three-dimensional reference data including the information about the surface of the object by performing first segmentation on the volumetric data and may identify regions corresponding to a plurality of teeth included in the object by performing second segmentation on the three-dimensional reference data.

The three-dimensional data obtaining device 300 according to an embodiment may generate an object image from the three-dimensional reference data and display the object image.

FIGS. 5A and 5B illustrate an example of a screen on which the three-dimensional data obtaining device 300 displays an object image 510 generated from the three-dimensional reference data, according to an embodiment. For example, the object image may be represented to be semi-transparent or in a gray scale.

Next, the three-dimensional data obtaining device 300 according to an embodiment may select a first point on the three-dimensional reference data. The three-dimensional data obtaining device 300 according to an embodiment may display, on an object image, the first point selected on the three-dimensional reference data.

The three-dimensional data obtaining device 300 according to an embodiment may select the first point as an initial position to align the three-dimensional reference data with scan data scanned by an optical three-dimensional scanner. For example, the first point may be used as an initial value for aligning the three-dimensional reference data with the scan data by using an ICP algorithm.

For example, the three-dimensional data obtaining device 300 may select a position corresponding to one voxel from among voxels included in the three-dimensional reference data as the first point. Alternatively, the three-dimensional data obtaining device 300 may select a position corresponding to one voxel from among the voxels included in the three-dimensional reference data and peripheral voxels as the first point. Alternatively, the three-dimensional data obtaining device 300 may select a position corresponding to one tooth from among a plurality of teeth included in the object as the first point.

The three-dimensional data obtaining device 300 according to an embodiment may receive a user input for selecting the first point or may automatically select the first point.

For example, the three-dimensional data obtaining device 300 according to an embodiment may select the first point on the three-dimensional reference data, based on the user input. The three-dimensional data obtaining device 300 may receive a user input with respect to the displayed object image and may select a position on the three-dimensional reference data, corresponding to the user input, as the first point.

The user may select the first point and may manipulate the optical three-dimensional scanner to scan an object region corresponding to the first point. The user may move the optical three-dimensional scanner around the object region corresponding to the first point.

As another example, the three-dimensional data obtaining device 300 according to an embodiment may automatically select the first point on the three-dimensional reference data, according to a predetermined reference. For example, the three-dimensional data obtaining device 300 may select the first point based on at least one of a result of analyzing the three-dimensional reference data, a medical record of a patient, a patient's plan for medical treatment, a past scanning record of a user, a user configuration, a value determined as default, or a scan purpose.

The three-dimensional data obtaining device 300 according to an embodiment may select a position corresponding to one tooth (for example, a left molar) predetermined from among the plurality of teeth included in the object, as the first point. For example, when the object is an oral cavity, the three-dimensional data obtaining device 300 may select different teeth as the first point according to a purpose of scanning the object via the optical three-dimensional scanner.

The three-dimensional data obtaining device 300 according to an embodiment may display, on the object image, the first point selected on the three-dimensional reference data. By referring to the object image on which the first point is displayed, the user may manipulate the optical three-dimensional scanner to scan an object region corresponding to the first point. The user may move the optical three-dimensional scanner around the object region corresponding to the first point.

Figure 6A:
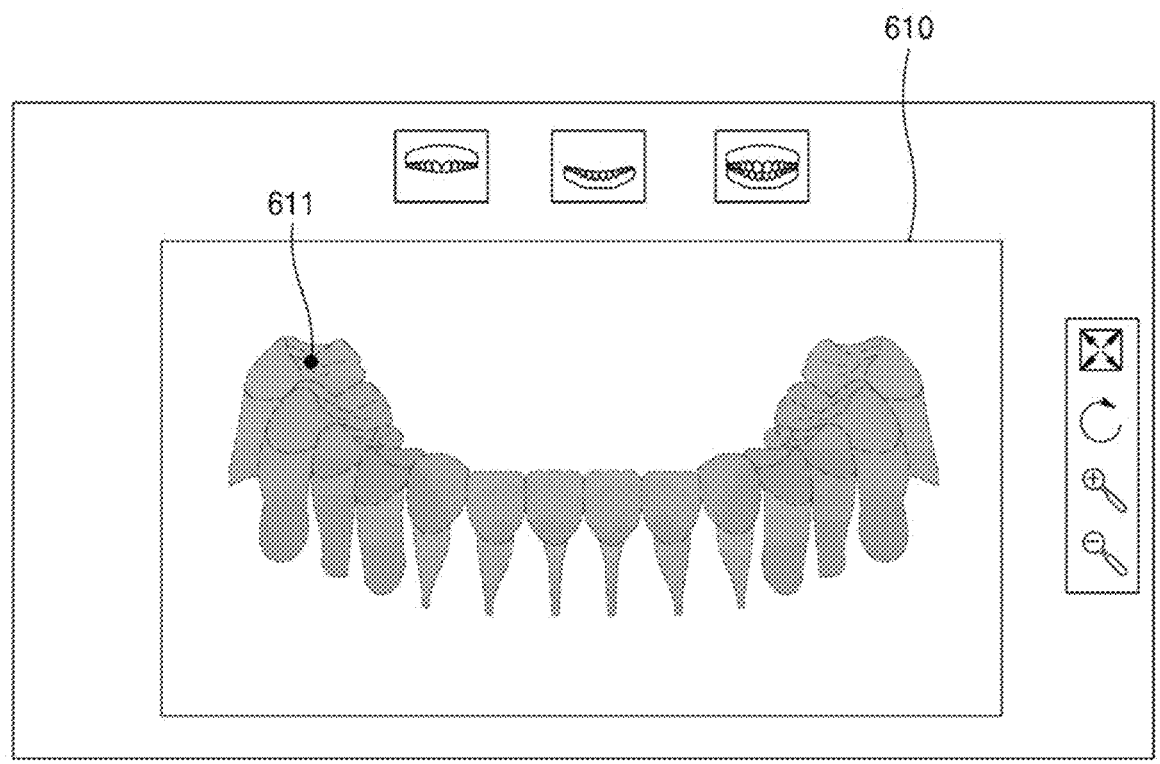
FIG. 6A illustrates an example of a screen on which a three-dimensional data obtaining device displays an object image indicating a first point selected on three-dimensional reference data, according to an embodiment.
Figure 6B:
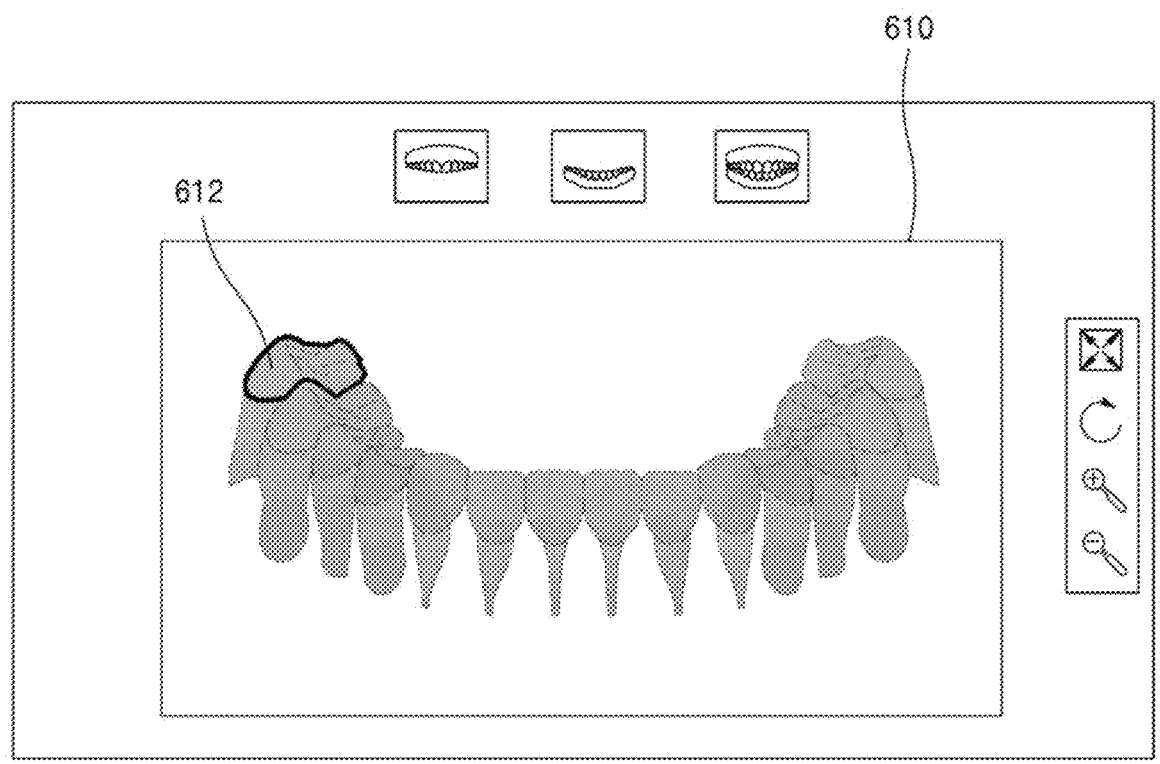
FIG. 6B illustrates an example of a screen on which a three-dimensional data obtaining device displays an object image indicating a first point selected on three-dimensional reference data, according to an embodiment.

FIGS. 6A and 6B illustrate an example of a screen on which the three-dimensional data obtaining device 300 displays an object image indicating a first point selected on three-dimensional reference data, according to an embodiment.

The three-dimensional data obtaining device 300 according to an embodiment may select a position corresponding to one voxel from among the voxels included in the three-dimensional reference data and peripheral voxels as the first point. As illustrated in FIG. 6A, the three-dimensional data obtaining device 300 may display a first point 611 on an object image 610.

Alternatively, the three-dimensional data obtaining device 300 according to an embodiment may select, as the first point, a position on the three-dimensional reference data on which segmentation is performed for each tooth, the position corresponding to one tooth from among a plurality of teeth included in an object. As illustrated in FIG. 6B, the three-dimensional data obtaining device 300 may select and display a point 612 corresponding to a predetermined tooth on the object image 610 as the first point.

When the three-dimensional data obtaining device 300 according to an embodiment displays, on the object image, the first point selected on the three-dimensional reference data, the user may move the optical three-dimensional scanner around an object region corresponding to the first point. The optical three-dimensional scanner may scan the object region corresponding to the first point to obtain the first frame as an initial value.

In operation S420, the three-dimensional data obtaining device 300 according to an embodiment of the disclosure may obtain the first frame obtained by scanning the object. The three-dimensional data obtaining device 300 may obtain the first frame obtained by scanning the first region of the object corresponding to the first point.

The three-dimensional data obtaining device 300 according to an embodiment may obtain the first frame including shape information about a surface of the object via the optical three-dimensional scanner. For example, the three-dimensional data obtaining device 300 may obtain, in a wired or wireless manner, raw data from the optical three-dimensional scanner using a structured light with stereo vision method and may reconfigure the raw data into the first frame according to an optical triangulation method. With respect to a detailed method, performed by the three-dimensional data obtaining device 300, of obtaining the scan data of the object, according to an embodiment, the descriptions of FIGS. 2 and 3 may be applied In operation S430, the three-dimensional data obtaining device 300 according to an embodiment of the disclosure may align the first frame on the three-dimensional reference data based on the first point.

The three-dimensional data obtaining device 300 according to an embodiment may determine a three-dimensional coordinate value of the first frame, based on a three-dimensional coordinate value of the first point on the three-dimensional reference data selected in operation S410. The three-dimensional data obtaining device 300 may determine an initial position of the first frame as close as possible to the first point on the three-dimensional reference data selected in operation S410. The first point selected on the three-dimensional reference data may indicate a region greater than a region of the object indicated by the first frame. For example, one tooth on the three-dimensional reference data may be selected as the first point, and the first frame obtained by scanning a region of the corresponding tooth may be obtained. In this case, the three-dimensional data obtaining device 300 may determine the initial position of the first frame such that the three-dimensional coordinate value of the first point and the three-dimensional coordinate value of the first frame become as close to each other as possible. The three-dimensional data obtaining device 300 may align the first frame on the first point on the three-dimensional reference data based on the determined initial position.

The three-dimensional data obtaining device 300 according to an embodiment may use various algorithms for aligning the three-dimensional reference data and the first frame. For example, an ICP algorithm may be used.

ICP is a method of aligning two different pieces of three-dimensional data by minimizing a distance deviation. A detailed process of performing the ICP is described above with reference to S402 of FIG. 4, and thus, the same description is omitted.

In operation S440, the three-dimensional data obtaining device 300 according to an embodiment of the disclosure may obtain a second frame obtained by scanning the object.

The three-dimensional data obtaining device 300 according to an embodiment may obtain, in real time, frames obtained by scanning operations of the optical three-dimensional scanner performed in a predetermined time interval. The first frame and the second frame may be obtained by the optical three-dimensional scanner moved by a user. The second frame may indicate the second region having at least a portion overlapping the first region of the object indicated by the first frame.

In operation S450, the three-dimensional data obtaining device 300 according to an embodiment of the disclosure may align the second frame on the three-dimensional reference data.

The three-dimensional data obtaining device 300 may align the second frame on the three-dimensional reference data based on the three-dimensional coordinate value of the aligned first frame.

The three-dimensional coordinate value of the first frame may denote a coordinate value indicating a position of the first frame determined by aligning the first frame on the three-dimensional reference data on a three-dimensional domain. A detailed method, performed by the three-dimensional data obtaining device 300, of aligning the second frame on the three-dimensional reference data based on the three-dimensional coordinate value of the first frame, according to an embodiment, is described above with respect to operation S403 of FIG. 4A and with reference to FIG. 4B, and thus, the same description is omitted.

The three-dimensional data obtaining device 300 may obtain three-dimensional data by merging the aligned first frame with the second frame, based on the three-dimensional reference data.

As described above, the three-dimensional data obtaining device 300 according to an embodiment may align each of obtained frames based on the three-dimensional reference data, and thus, may align the frames on accurate positions of the object without distortion of a curvature of a dental arch, and the three-dimensional data obtaining device 300 according to an embodiment may merge the aligned frames based on the overlapping region, to finally obtain the three-dimensional data.

Here, the merging between the frames may include both of real time alignment in which whenever a frame is obtained, the frame is merged with a previously obtained frame, and global alignment in which all frames that are obtained are merged at once after a completion of scanning operations. For example, in the case of real time alignment, when a first frame, a second frame, and a third frame, which are consecutive to each other, are obtained, alignment between the first frame and the second frame may be performed, and alignment between the second frame and the third frame may be performed. However, in the case of global alignment, alignment among all of the frames may be performed. That is, alignment may be performed between the first frame and the second frame, between the second frame and the third frame, or between the first frame and the third frame. The ICP algorithm may be used for merging between the frames. However, the disclosure is not limited thereto, and various algorithms may be used.

The three-dimensional data obtaining device 300 according to an embodiment of the disclosure may merge the first frame with the second frame on an optimal position, by taking into account the three-dimensional reference data and the aligned first frame.

The three-dimensional data obtaining device 300 according to an embodiment may determine whether or not the second frame may be aligned on the three-dimensional reference data by comparing the three-dimensional reference data with the second frame, based on the three-dimensional coordinate value of the first frame. When the second frame may be aligned on the three-dimensional reference data, the three-dimensional data obtaining device 300 according to an embodiment may align the second frame on the three-dimensional reference data. When the second frame may not be aligned on the three-dimensional reference data, the three-dimensional data obtaining device 300 may merge the second frame with the aligned first frame to overlap the aligned first frame. A method of obtaining the three-dimensional data according to an embodiment will be described in more detail below with reference to FIG. 9.

The three-dimensional data obtaining device 300 according to another embodiment may determine whether or not the second frame may be aligned on the first frame. The three-dimensional data obtaining device 300 may determine whether or not the second frame may be aligned on the first frame by comparing the first frame with the second frame.

When the second frame may be aligned on the first frame, the three-dimensional data obtaining device 300 may merge the second frame with the first frame to overlap the first frame.

When the second frame may not be aligned on the first frame, the three-dimensional data obtaining device 300 may align the second frame on the three-dimensional reference data based on the three-dimensional coordinate value of the first frame. A method of obtaining the three-dimensional data according to another embodiment will be described in more detail below with reference to FIG. 10.

The three-dimensional data obtaining device 300 according to an embodiment may display, on an object image, the three-dimensional data obtained by merging (or aligning) the frames obtained by scanning the object in a predetermined time interval.

As described above, the three-dimensional data obtaining device 300 according to an embodiment of the disclosure may obtain the three-dimensional data by merging the first frame obtained by selecting the first point and scanning the first region corresponding to the selected first point with the second frame obtained by scanning the second region having at least a portion overlapping the first region.

Also, the three-dimensional data obtaining device 300 according to an embodiment of the disclosure may further obtain the three-dimensional data by merging a third frame obtained by selecting a second point and scanning a third region corresponding to the selected second point with a fourth frame obtained by scanning a fourth region having at least a portion overlapping the third region.

The first point and the second point may be points designating discontinuous regions, points designating close regions, or points designating different positions with respect to the same region.

For example, the three-dimensional data obtaining device 300 may select a first tooth as the first point and may merge frames (for example, the first frame, the second frame, etc.) obtained by scanning one or more portions or a section of the first tooth to obtain three-dimensional data with respect to the first tooth. Next, the three-dimensional data obtaining device 300 may select a second tooth adjacent to the first tooth as the second point and may merge frames (for example, the third frame, the fourth frame, etc.) obtained by scanning one or more portions or a section of the second tooth to obtain three-dimensional data with respect to the second tooth.

Alternatively, for example, the three-dimensional data obtaining device 300 may select one or more portions or a section of the first tooth as the first point and may merge frames (for example, the first frame, the second frame, etc.) obtained by scanning the portions corresponding to the first point to obtain three-dimensional data with respect to the corresponding portions or the corresponding section of the first tooth. Next, the three-dimensional data obtaining device 300 may select an adjacent portion or an adjacent section of the first tooth as the second point and may merge frames (for example, the third frame, the fourth frame, etc.) obtained by scanning the adjacent portion or the adjacent section of the first tooth to obtain three-dimensional data with respect to the adjacent portion or the adjacent section of the first tooth.

Alternatively, for example, the three-dimensional data obtaining device 300 may select the first tooth as the first point and may merge frames (for example, the first frame, the second frame, etc.) obtained by scanning one or more portions or a section of the first tooth to obtain three-dimensional data with respect to the first tooth. Next, the three-dimensional data obtaining device 300 may select the second tooth apart from the first tooth by a distance greater than or equal to a predetermined distance as the second point and may merge frames (for example, the third frame, the fourth frame, etc.) obtained by scanning one or more portions or a section of the second tooth to obtain three-dimensional data with respect to the second tooth.

Figure 7:
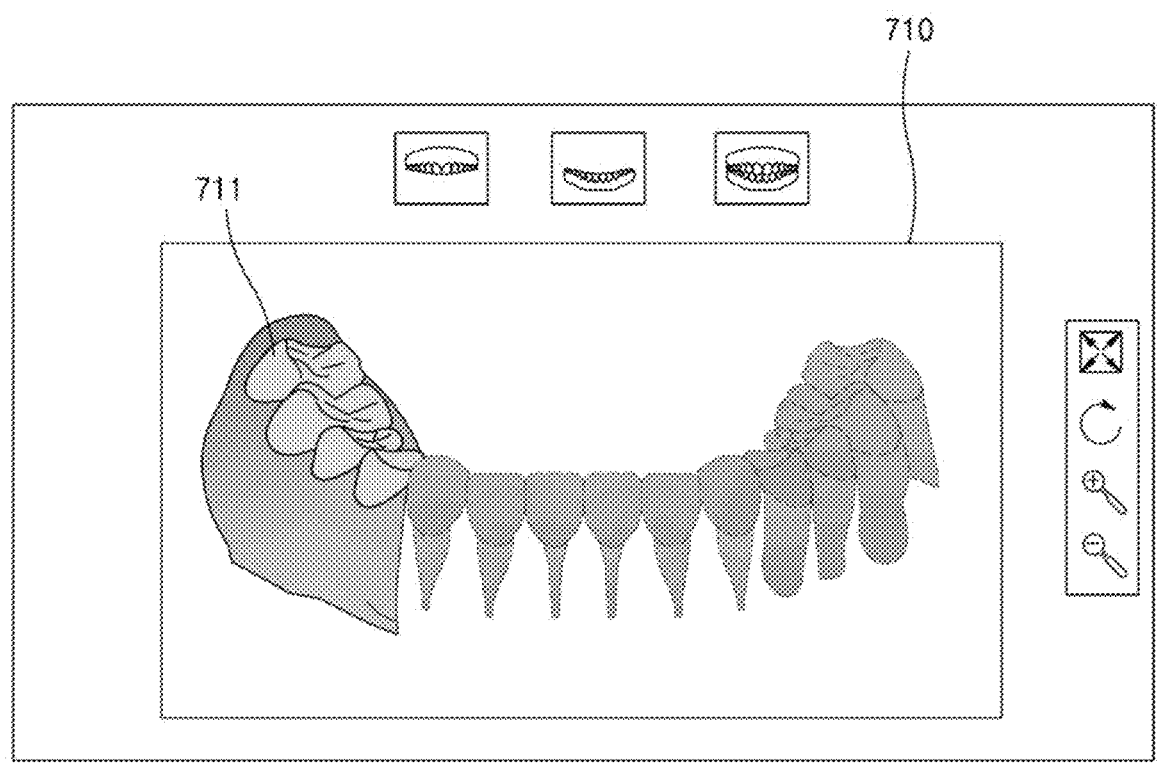
FIG. 7 illustrates an example of a screen on which a three-dimensional data obtaining device displays three-dimensional data obtained in real time, according to an embodiment.

FIG. 7 illustrates an example of a screen 710 on which the three-dimensional data obtaining device displays three-dimensional data obtained in real time, according to an embodiment.

While a user manipulates the optical three-dimensional scanner to move around the first point of the object, the optical three-dimensional scanner may scan the object in a predetermined time interval. The three-dimensional data obtaining device 300 may merge the frames obtained from the optical three-dimensional scanner to obtain three-dimensional data 711. The three-dimensional data obtaining device 300 according to an embodiment may obtain the three-dimensional data 711 with respect to the first region of the object based on the first point and may display the three-dimensional data 711.

Figure 8A:
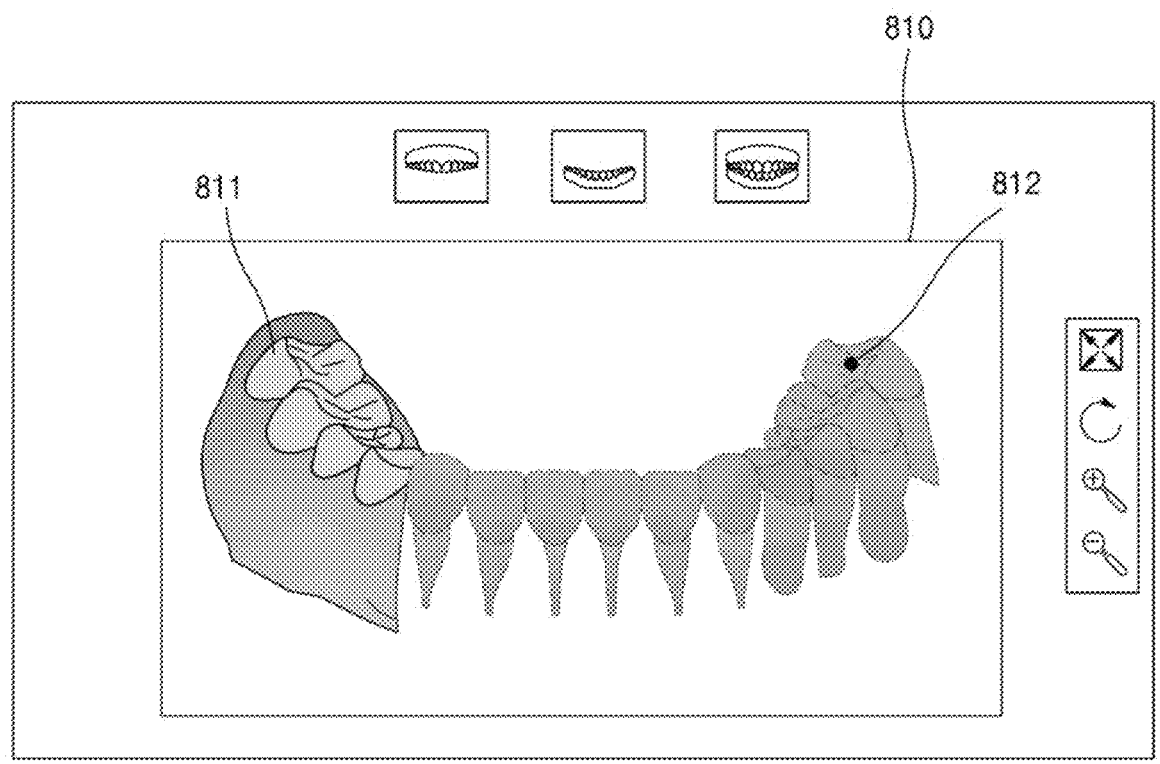
FIG. 8A illustrates an example of a screen on which a three-dimensional data obtaining device displays an object image indicating a second point selected on three-dimensional reference data, according to an embodiment.

FIG. 8A illustrates an example of a screen 810 on which the three-dimensional data obtaining device displays an object image indicating the second point selected on the three-dimensional reference data, according to an embodiment.

As illustrated in FIG. 8A, the three-dimensional data obtaining device 300 according to an embodiment may obtain and display three-dimensional data 811 with respect to the first region of the object based on the first point selected based on a user input. When an operation of scanning the first region is completed, a user may select a second point 812 and may manipulate the optical three-dimensional scanner to move around the second point of the object. While the user manipulates the optical three-dimensional scanner to move around the second point of the object, the optical three-dimensional scanner may scan the object in a predetermined time interval.

For example, the three-dimensional data obtaining device 300 according to an embodiment may select the second point on the three-dimensional reference data and may obtain a third frame by scanning a region of the object corresponding to the second point. The three-dimensional data obtaining device 300 may align the third frame on the three-dimensional reference data based on the second point. The three-dimensional data obtaining device 300 may obtain a fourth frame and may align the fourth frame based on a three-dimensional coordinate value of the third frame to obtain three-dimensional data.

With respect to a detailed method, performed by the three-dimensional data obtaining device 300, of aligning the fourth frame on the three-dimensional reference data based on the three-dimensional coordinate value of the third frame, according to an embodiment, the descriptions with respect to operation S403 of FIG. 4A, operation S450 of FIG. 4C, or the description with reference to FIG. 4B may be applied. The same description is omitted.

Figure 8B:
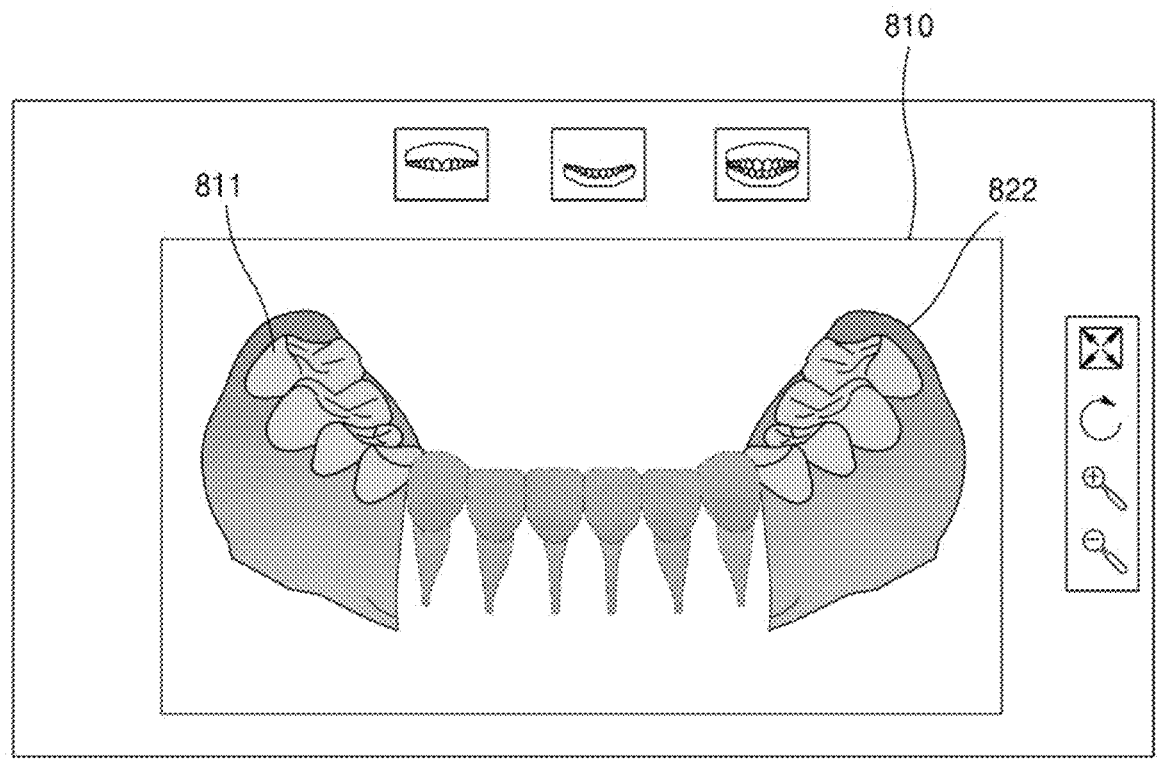
FIG. 8B illustrates an example of a screen on which a three-dimensional data obtaining device displays three-dimensional data obtained in real time based on a second point, according to an embodiment.

FIG. 8B illustrates an example of a screen 810 on which the three-dimensional data obtaining device 300 displays three-dimensional data obtained in real time based on the second point, according to an embodiment.

The three-dimensional data obtaining device 300 according to an embodiment may obtain three-dimensional data 822 by merging frames obtained from the optical three-dimensional scanner based on the second point selected based on a user input. As illustrated in FIG. 8B, according to an embodiment of the disclosure, by aligning the frames scanned in real time based on the three-dimensional reference data, the three-dimensional data with respect to discontinuous regions 811 and 822 may be obtained.

As described above, according to an embodiment of the disclosure, when the three-dimensional data obtaining device 300 reconfigures the three-dimensional data based on frames obtained from the optical three-dimensional scanner, the three-dimensional reference data may be used for the aligning to easily reconfigure the three-dimensional data including information about discontinuous regions.

According to previous methods, a process of scanning the entire object was required, even when three-dimensional data with respect to only some regions included in an object was needed. For example, in order to obtain three-dimensional data about molars at both sides of lower jaws for prosthetic dentistry for the molars at both sides, it was needed to scan all of the teeth in the lower jaws from the molar at one side to the molar at the other side by using an optical three-dimensional scanner. That is, according to the previous methods not using additional reference data, when the optical three-dimensional scanner moves to a right molar region in a short time period after scanning a left molar region, to scan the right molar region, based on a user manipulation, it was impossible to reconfigure proper three-dimensional data with only scan data with respect to the two regions having no overlapping section.

However, the three-dimensional data obtaining device 300 according to a disclosed embodiment, even when discontinuous regions are scanned by the optical three-dimensional scanner, scan frames may be aligned based on the three-dimensional reference data, and thus, three-dimensional data accurately reflecting a shape of an object may be obtained.

Figure 9:
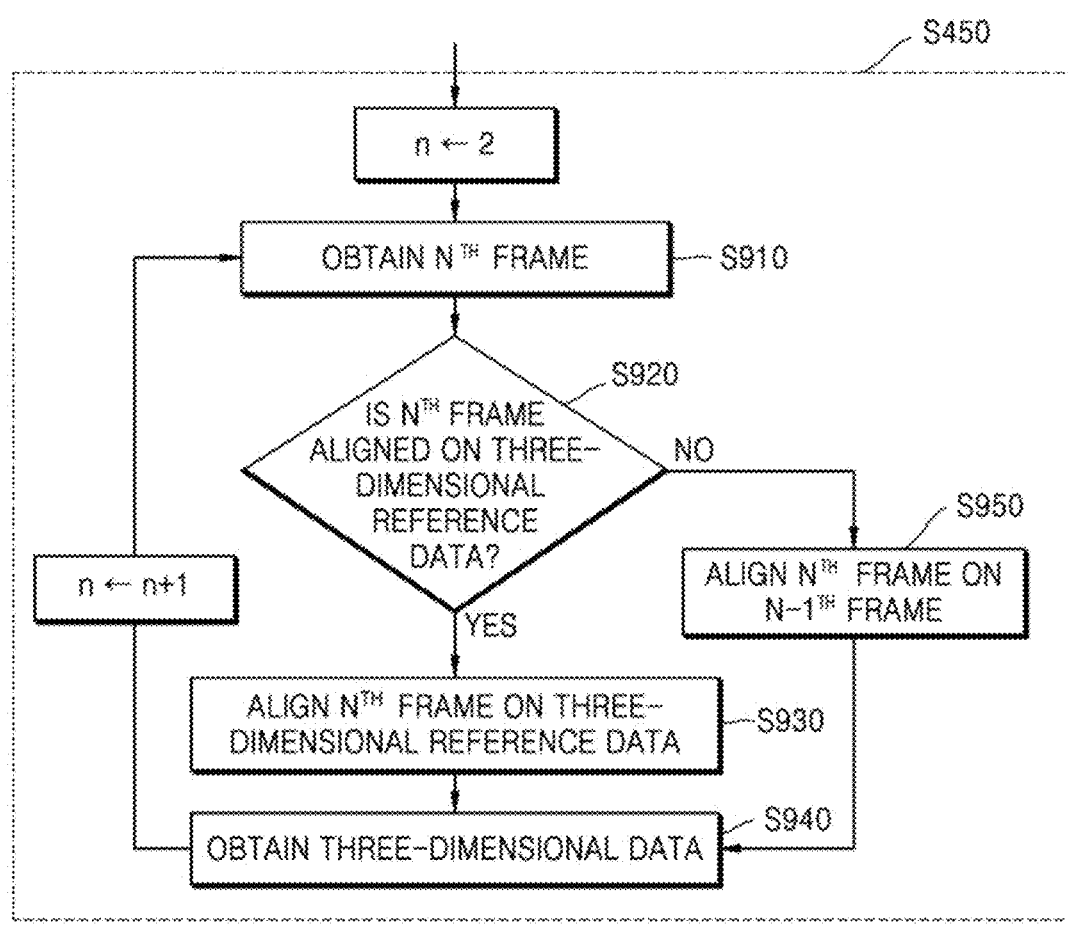
FIG. 9 is a flowchart of a method of obtaining three-dimensional data according to an embodiment.
Figure 10:
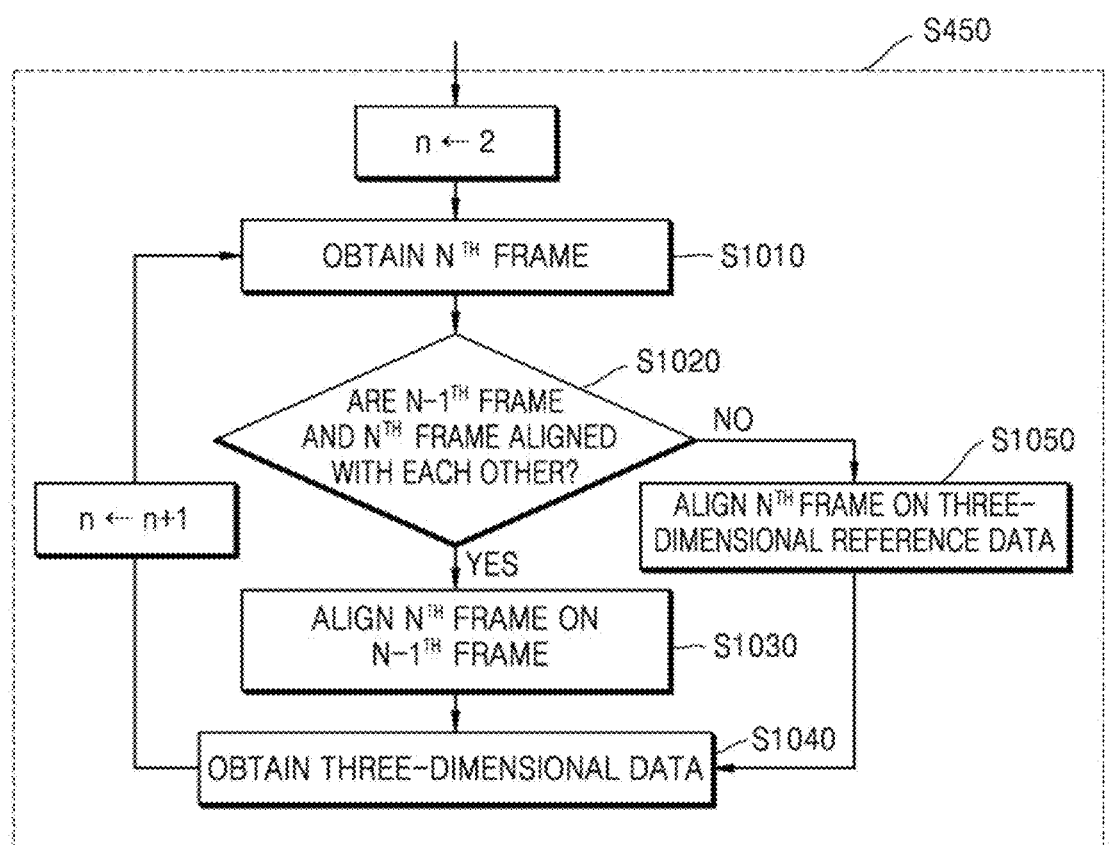
FIG. 10 is a flowchart of a method of obtaining three-dimensional data according to an embodiment.

Hereinafter, referring to FIGS. 9 and 10, a detailed method, performed by the three-dimensional data obtaining device 300, of obtaining three-dimensional data by aligning scan data obtained in real time on the three-dimensional reference data, is described, according to an embodiment. FIGS. 9 and 10 illustrate an operation order when the three-dimensional data obtaining device 300 obtains an $n^{th}$ frame (n≥2, wherein n is an integer), after a first frame is aligned based on a first point selected on the three-dimensional reference data. FIGS. 9 and 10 may show flowcharts illustrating operation S450 of FIG. 4C in detail, and thus, the same description as FIG. 4C is omitted.

The three-dimensional data obtaining device 300 according to an embodiment may align the frames on the three-dimensional reference data as the frames obtained by scanning an object are obtained in real time, to update three-dimensional data and obtain the updated three-dimensional data.

FIG. 9 is a flowchart of a method of obtaining three-dimensional data according to an embodiment.

In operation S910, the three-dimensional data obtaining device 300 according to an embodiment may obtain an $n^{th}$ frame obtained by scanning an object. Here, n may be an integer greater than or equal to 2.

In operation S920, the three-dimensional data obtaining device 300 according to an embodiment may determine whether or not the $n^{th}$ frame is aligned on the three-dimensional reference data. The three-dimensional data obtaining device 300 may determine whether or not the $n^{th}$ frame is aligned on the three-dimensional reference data by comparing the $n^{th}$ frame with the three-dimensional reference data, based on a three-dimensional coordinate value of an $n-1^{th}$ frame. The three-dimensional data obtaining device 300 may determine whether or not the $n^{th}$ frame may be aligned around the $n-1^{th}$ frame aligned on the three-dimensional reference data.

For example, when the three-dimensional reference data is data that is segmented to include only data with respect to a tooth, a second frame may be aligned on the three-dimensional reference data when the second frame capturing a surface of the tooth via the optical three-dimensional scanner is received. However, when the second frame capturing a region corresponding to the gum via the optical three-dimensional scanner is received, the second frame may not be aligned on the three-dimensional reference data in which information about the gum is not included and only information about the surface of the tooth is included.

Thus, the three-dimensional data obtaining device 300 according to an embodiment may determine whether the second frame is aligned on the three-dimensional reference data by comparing the three-dimensional reference data with the second frame.

For example, the three-dimensional data obtaining device 300 may determine whether or not the $n^{th}$ frame is aligned on the three-dimensional reference data based on a difference of distance values between apexes extracted from the three-dimensional reference data and corresponding points extracted from the $n^{th}$ frame. The three-dimensional data obtaining device 300 according to an embodiment may not determine that the $n^{th}$ frame is aligned on the three-dimensional reference data, when the difference of the distance values between the apexes and the corresponding points is equal to or greater than a threshold value.

As another example, the three-dimensional data obtaining device 300 may determine whether or not the $n^{th}$ frame is aligned on the three-dimensional reference data by comparing the three-dimensional reference data with a shape of the $n^{th}$ frame. The three-dimensional data obtaining device 300 may compare voxels or meshes included in the three-dimensional reference data with voxels or meshes included in the $n^{th}$ frame, and may determine that the $n^{th}$ frame may not be aligned on the three-dimensional reference data, when a shape difference has a value greater than or equal to a predetermined value. However, the three-dimensional data obtaining device 300 may determine that the $n^{th}$ frame may be aligned on the three-dimensional reference data, when the shape difference has a value less than the predetermined value.

In operation S930, the three-dimensional data obtaining device 300 according to an embodiment may align the $n^{th}$ frame on the three-dimensional reference data, when it is determined that the $n^{th}$ frame may be aligned with respect to the three-dimensional reference data.

However, in operation S950, the three-dimensional data obtaining device 300 according to an embodiment may align the $n^{th}$ frame on the $n-1^{th}$ frame previously obtained, when it is determined that the $n^{th}$ frame may not be aligned with respect to the three-dimensional reference data. To align the $n^{th}$ frame on the $n-1^{th}$ frame may denote to merge the $n^{th}$ frame with respect to the $n-1^{th}$ frame such that corresponding regions between the $n-1^{th}$ frame and the $n^{th}$ frame may overlap each other.

In operation S940, the three-dimensional data obtaining device 300 according to an embodiment may obtain the three-dimensional data by additionally merging the aligned $n^{th}$ frame with the three-dimensional data obtained by merging the first frame to the $n-1^{th}$ frame.

FIG. 10 is a flowchart of a method of obtaining three-dimensional data according to an embodiment.

In operation S1010, the three-dimensional data obtaining device 300 according to an embodiment may obtain the $n^{th}$ frame obtained by scanning an object. Here, n may be an integer greater than or equal to 2.

In operation S1020, the three-dimensional data obtaining device 300 according to an embodiment may determine whether or not the $n^{th}$ frame may be aligned with respect to the $n-1^{th}$ frame.

The three-dimensional data obtaining device 300 according to an embodiment may determine whether or not the $n^{th}$ frame may be aligned on the $n-1^{th}$ frame by comparing the $n^{th}$ frame with the $n-1^{th}$ frame. The three-dimensional data obtaining device 300 according to an embodiment may determine whether or not the $n^{th}$ frame may be aligned on the $n-1^{th}$ frame, based on an overlapped degree between the $n^{th}$ frame and the $n-1^{th}$ frame.

For example, when an object region captured by the $n-1^{th}$ frame and an object region captured by the $n^{th}$ frame sufficiently overlap each other (that is, overlap each other by a degree greater than or equal to a threshold rate), the $n^{th}$ frame may be aligned on the $n-1^{th}$ frame. However, when the object region captured by the $n-1^{th}$ frame and the object region captured by the $n^{th}$ frame do not sufficiently overlap each other (that is, overlap each other by a degree less than the threshold rate), the $n^{th}$ frame may not be aligned on the $n-1^{th}$ frame.

In operation S1030, the three-dimensional data obtaining device 300 according to an embodiment may align the $n^{th}$ frame on the $n-1^{th}$ frame, when it is determined that the $n^{th}$ frame may be aligned with respect to the $n-1^{th}$ frame.

However, in operation S1050, the three-dimensional data obtaining device 300 according to an embodiment may align the $n^{th}$ frame on the three-dimensional reference data based on a three-dimensional coordinate value of the $n-1^{th}$ frame, when it is determined that the $n^{th}$ frame may not be aligned with respect to the $n-1^{th}$ frame.

In operation S1040, the three-dimensional data obtaining device 300 according to an embodiment may obtain the three-dimensional data by merging the $n^{th}$ frame with the three-dimensional data obtained by merging the first frame to the $n-1^{th}$ frame.

Figure 11:
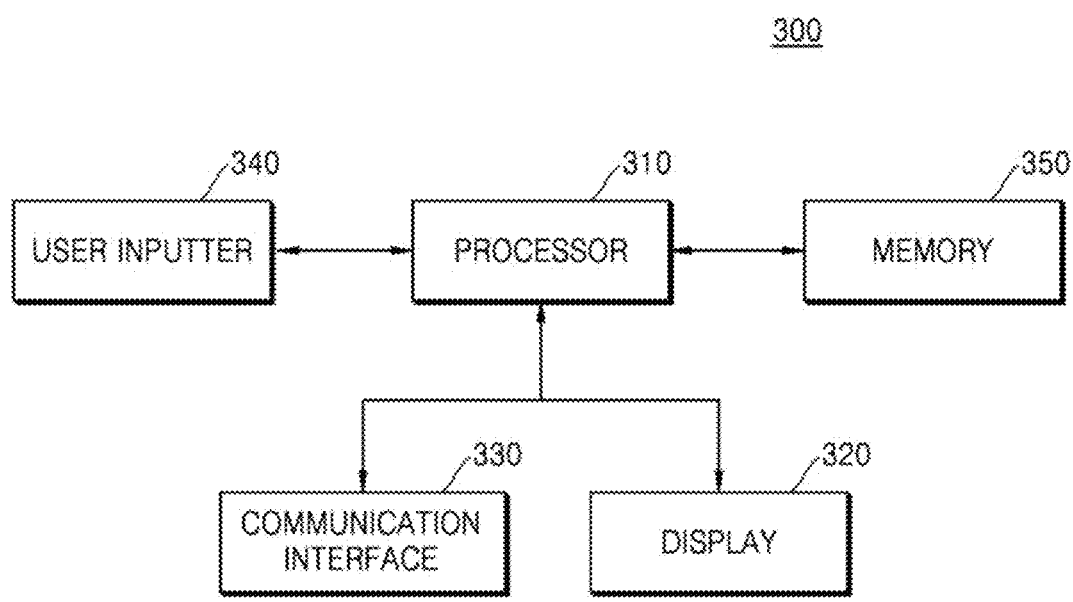
FIG. 11 is a block diagram of a three-dimensional data obtaining device, according to an embodiment.

FIG. 11 is a block diagram of a three-dimensional data obtaining device, according to an embodiment.

The block diagram of the three-dimensional data obtaining device 300 illustrated in FIG. 11 is an example of the three-dimensional data obtaining device 300 described above. The three-dimensional data obtaining device 300 illustrated in FIG. 11 may perform the method of obtaining the three-dimensional data according to various embodiments of the disclosure, and may apply the descriptions with reference to FIGS. 1 to 10. Thus, the same descriptions as described above are omitted.

The three-dimensional data obtaining device 300 according to various embodiments of the disclosure may be a stationary terminal or a mobile terminal. For example, the three-dimensional data obtaining device 300 may include a computing device, such as a smartphone, a laptop computer, a desk top computer, a PDA, a tablet PC, etc., but is not limited thereto.

Referring to FIG. 11, the three-dimensional data obtaining device 300 may include a processor 310, the display 320, a communication interface 330, a user inputter 340, and a memory 350.

The processor 310 according to an embodiment may execute at least one instruction to control the three-dimensional data obtaining device 300 to perform a desired operation. Here, the at least one instruction may be stored in a built-in memory (not shown) included in the processor 310 or may be stored in the memory 350 included in the three-dimensional data obtaining device 300 separately from the processor 310.

The processor 310 according to an embodiment may execute the at least one instruction to control one or more components included in the three-dimensional data obtaining device 300 to perform desired operations. Thus, even when an example in which the processor 310 performs a predetermined operation is described, it may denote that one or more components included in the three-dimensional data obtaining device 300 are controlled by the processor 310 to perform the predetermined operation.

The processor 310 according to an embodiment may include random-access memory (RAM) (not shown) that stores a signal or data received from the outside of the three-dimensional data obtaining device 300 or is used as a storage area corresponding to various jobs performed by the three-dimensional data obtaining device 300, read-only memory (ROM) (not shown) storing a control program and/or a plurality of instructions for controlling operations by the three-dimensional data obtaining device 300, and at least one internal processor (not shown) configured to execute at least one instruction.

Also, the processor 310 may include a graphic processing unit (GPU) (not shown) for processing graphics data corresponding to video data. Also, the processor 310 may be implemented as a system on chip (SoC) in which a core (not shown) and a GPU (not shown) are combined with each other.

According to a disclosed embodiment, the processor 310 may generate three-dimensional data with respect to an object based on data received from an optical three-dimensional scanner and may generate a three-dimensional image with respect to the object.

The display 320 may display a predetermined screen according to control by the processor 310. In detail, the display 320 may display a UI screen including an image generated based on data obtained by an optical three-dimensional scanner (for example, 100 of FIG. 3) by scanning an object. Alternatively, the display 320 may display a UI screen including information associated with diagnosis and treatment with respect to an object.

The communication interface 330 may perform communication with at least one external electronic device (not shown) through a wired or wireless communication network. In detail, the communication interface 330 may perform communication with the optical three-dimensional scanner according to control by the processor 310.

The user inputter 340 may receive a user input for controlling the three-dimensional data obtaining device 300. The user inputter 340 may include a user input device including a touch panel configured to sense a touch of a user, a button configured to receive a push manipulation of the user, a mouse or a keyboard configured to indicate or select a point on a UI screen, or the like, but is not limited thereto.

Also, the user inputter 340 may include a sound recognition device (not shown) for sound recognition. For example, the sound recognition device may include a microphone. The sound recognition device may receive a user's voice command or voice request. Thus, the processor 310 may perform a control operation such that an operation corresponding to the voice command or the voice request may be performed.

The memory 350 may store at least one instruction. Also, the memory 350 may store at least one instruction executed by the processor 310. Also, the memory 350 may store at least one program executed by the processor 3410. The memory 350 may store data (for example, raw data obtained by scanning an object) received from the optical three-dimensional scanner. The memory 350 may store volumetric data of an object obtained by CT or MRI or three-dimensional reference data including information with respect to a surface of the object extracted from the corresponding volumetric data. The memory 350 may store an object image three-dimensionally representing an object.

The processor 310 according to an embodiment of the disclosure may execute the program stored in the memory 350 to control general operations of the three-dimensional data obtaining device 300. The processor 310 may control other components included in the three-dimensional data obtaining device 300 in order to obtain three-dimensional data with respect to an object.

With respect to a detailed method, performed by the processor 310, of obtaining the three-dimensional data by controlling the general operations of the three-dimensional data obtaining device 300, the descriptions with reference to FIGS. 4A and 4C may be applied, and the same descriptions are omitted.

The processor 310 according to an embodiment may obtain three-dimensional reference data with respect to the object. The three-dimensional reference data according to an embodiment may be surface data of the object, extracted from volumetric data obtained by CT or MRI. The processor 310 may perform segmentation on the volumetric data obtained by CT or MRI, to obtain the three-dimensional reference data including information about a surface of the object.

The processor 310 according to an embodiment may obtain a first frame obtained by scanning a first region of the object via an optical three-dimensional scanner and align the first frame on the three-dimensional reference data. The processor 310 may obtain a second frame obtained by scanning a second region of the object, at least a portion of the second region overlapping the first region, and may align the second frame on the three-dimensional reference data. The processor 310 may align the second frame on the three-dimensional reference data based on a three-dimensional coordinate value of the aligned first frame. The processor 310 may obtain the three-dimensional data by merging the first frame with the second frame based on the overlapping portion.

The processor 310 according to an embodiment may select a first point on the three-dimensional reference data and obtain the first frame obtained by scanning the first region corresponding to the selected first point.

For example, the processor 310 may select the first point on the three-dimensional reference data based on a user input. The processor 310 may select a point corresponding to one tooth from among a plurality of teeth included in the object as the first point on the three-dimensional reference data.

As another example, the processor 310 may automatically select the first point on the three-dimensional reference data.

The processor 310 according to an embodiment may control the display 320 to display an object image generated from the three-dimensional reference data with respect to the object and to display, on the object image, the first point selected on the three-dimensional reference data.

The processor 310 according to an embodiment may obtain the first frame obtained by scanning a region of the object corresponding to the first point via the optical three-dimensional scanner and may align the first frame on the three-dimensional reference data based on the first point. The first frame may include shape information about the surface of the object obtained by the optical three-dimensional scanner.

The processor 310 according to an embodiment may extract a plurality of apexes on the three-dimensional reference data based on the first point, extract a plurality of corresponding points respectively corresponding to the plurality of apexes from the first frame, and align the first frame on the three-dimensional reference data based on a difference of distance values between the plurality of apexes and the plurality of corresponding points.

The processor 310 may obtain the second frame obtained by scanning the object via the optical three-dimensional scanner. The optical three-dimensional scanner may obtain the second frame obtained by scanning the second region having at least a portion overlapping the first region of the object, the first region being indicated by the first frame.

The processor 310 may obtain the three-dimensional data by aligning the second frame on the three-dimensional reference data based on a coordinate value of the aligned first frame.

For example, the processor 310 may determine whether or not the second frame may be aligned on the three-dimensional reference data based on the three-dimensional coordinate value of the first frame. The processor 310 may align the second frame on the three-dimensional reference data, when the second frame may be aligned on the three-dimensional reference data. The processor 310 according to an embodiment may merge the second frame with the aligned first frame to overlap the aligned first frame, when the second frame may not be aligned on the three-dimensional reference data.

As another example, the processor 310 may determine whether or not the second frame may be aligned on the aligned first frame. When the second frame may be aligned on the aligned first frame, the processor 310 may merge the second frame with the aligned first frame to overlap the aligned first frame. When the second frame may not be aligned on the aligned first frame, the processor 310 may merge the second frame with the three-dimensional reference data, based on the three-dimensional coordinate value of the aligned first frame.

The processor 310 according to an embodiment may control the display 320 to display, on the object image, the three-dimensional data obtained by merging the frames obtained by scanning the object in a predetermined time interval.

Also, the processor 310 according to an embodiment may select the second point on the three-dimensional reference data and may obtain the third frame obtained by scanning a region of the object corresponding to the second point. The processor 310 may align the third frame on the three-dimensional reference data based on the second point. The processor 310 may obtain the fourth frame obtained by scanning the object. The processor 310 may obtain the three-dimensional data by aligning the fourth frame on the three-dimensional reference data based on a coordinate value of the aligned third frame.

Thus, the three-dimensional data obtaining device 300 according to an embodiment of the disclosure may obtain three-dimensional data with respect to regions including the object region around the first point and the object region around the second point.

The method of obtaining the three-dimensional data according to an embodiment of the disclosure may be realized in the form of a program command which may be executed by various computer devices and may be recorded on a computer-readable medium. Also, according to an embodiment of the disclosure, a computer-readable storage medium having recorded thereon one or more programs including at least one instruction executing the method of obtaining the three-dimensional data may be provided.

The computer-readable medium may include a program command, a data file, a data structure, etc. individually or in a combined fashion. Here, examples of the computer-readable storage medium include magnetic media, such as hard discs, floppy discs, and magnetic tapes, optical media, such as compact disc-read only memories (CD-ROMs) and digital versatile discs (DVDs), magneto-optical media, such as floptical discs, and hardware devices configured to store and execute program commands, such as ROMs, RAMs, and flash memories.

Here, a machine-readable storage medium may be provided in a form of a non-transitory storage medium. Here, the "non-transitory storage medium" may denote a tangible storage medium. Also, the "non-transitory storage medium" may include a buffer in which data is temporarily stored.

According to an embodiment, a method of displaying an oral cavity image according to various embodiments disclosed in the present specification may be provided by being included in a computer program product. The computer program project may be distributed in the form of a device-readable storage medium (for example, CD-ROM). Alternatively, the computer program may be directly or through online distributed (e.g. download or upload) between two user devices (e.g., smartphones) through an application store (e.g. Play Store, etc.).

Although embodiments are described in detail above, the scope of the claims of the disclosure is not limited thereto, and various modifications and alterations by one of ordinary skill in the art using basic concept of the disclosure defined by the following claims are also included in the scope of the claims of the disclosure.

EXPLANATION OF REFERENCE NUMERALS

100: OPTICAL THREE-DIMENSIONAL SCANNER
310: PROCESSOR
320: DISPLAY
330: COMMUNICATION INTERFACE
340: USER INPUTTER
350: MEMORY

The invention claimed is:

1. A method of obtaining three-dimensional data, the method comprising:
   obtaining three-dimensional reference data with respect to an object, the three-dimensional reference data being surface data of the object extracted from volumetric data obtained by computed tomography (CT) or magnetic resonance imaging (MRI);
   aligning, on the three-dimensional reference data, a first frame obtained by scanning a first region of the object using an optical three-dimensional scanner;
   aligning, on the three-dimensional reference data, a second frame obtained by scanning a second region of the object using the optical three-dimensional scanner based on a three-dimensional coordinate value of the aligned first frame, at least a portion of the second region overlapping the first region; and
   obtaining the three-dimensional data by merging the first frame with the second frame based on an overlapping portion between the first region and the second region.

2. The method of claim 1, wherein the aligning of the first frame on the three-dimensional reference data comprises:
   selecting a first point on the three-dimensional reference data;
   obtaining the first frame by scanning the first region corresponding to the first point; and
   aligning the first frame on the three-dimensional reference data based on the first point.

3. The method of claim 2, wherein the aligning of the second frame on the three-dimensional reference data comprises aligning the second frame on the three-dimensional reference data based on the first point and a three-dimensional coordinate value of the aligned first frame.

4. The method of claim 2, further comprising:
   selecting a second point on the three-dimensional reference data;
   aligning, on the three-dimensional reference data, a third frame obtained by scanning a third region of the object corresponding to the second point;
   aligning, on the three-dimensional reference data, a fourth frame obtained by scanning a fourth region of the object, at least a portion of the fourth region overlapping the third region; and
   obtaining the three-dimensional data by merging the third frame with the fourth frame based on an overlapping portion between the third region and the fourth region.

5. The method of claim 2, wherein the selecting of the first point on the three-dimensional reference data comprises selecting the first point on the three-dimensional reference data based on a user input or selecting the first point on the three-dimensional reference data automatically.

6. The method of claim 2, wherein the selecting of the first point on the three-dimensional reference data further comprises selecting a point corresponding to one tooth from among a plurality of teeth included in the object as the first point on the three-dimensional reference data.

7. The method of claim 2, wherein the aligning of the first frame on the three-dimensional reference data comprises:
   extracting a plurality of apexes on the three-dimensional reference data based on the first point;
   extracting, from the first frame, a plurality of corresponding points respectively corresponding to the plurality of apexes; and
   aligning the first frame on the three-dimensional reference data, based on a difference of distance values between the plurality of apexes and the plurality of corresponding points.

8. The method of claim 1, further comprising displaying the three-dimensional data on an object image generated from the three-dimensional reference data.

9. The method of claim 1, further comprising:
   performing first segmentation on the volumetric data obtained by CT or MRI to obtain the three-dimensional reference data; and
   identifying a region corresponding to a plurality of teeth included in the object by performing second segmentation on the three-dimensional reference data.

10. The method of claim 1, wherein the first frame or the second frame is obtained by an optical three-dimensional scanner and comprises shape information about a surface of the object.

11. A device for obtaining three-dimensional data, the device comprising:
    a display;
    a communication interface including communication circuitry configured to communicate with an optical three-dimensional scanner; and
    at least one processor configured to control the three-dimensional data by executing at least one instruction, wherein the at least one processor is configured to:
    obtain three-dimensional reference data with respect to an object, the three-dimensional reference data being surface data of the object extracted from volumetric data obtained by computed tomography (CT) or magnetic resonance imaging (MRI);

obtain a first frame by scanning a first region of the object using the optical three-dimensional scanner and align the obtained first frame on the three-dimensional reference data;

obtain a second frame by scanning a second region of the object using the optical three-dimensional scanner based on a three-dimensional coordinate value of the aligned first frame, at least a portion of the second portion overlapping the first region, and align the obtained second frame on the three-dimensional reference data; and obtain the three-dimensional data by merging the first frame with the second frame based on an overlapping portion between the first portion and the second portion.

12. The device of claim 11, wherein the at least one processor is further configured to:

select a first point on the three-dimensional reference data;

obtain the first frame by scanning the first region corresponding to the first point; and align the first frame on the three-dimensional reference data based on the first point.

13. The device of claim 12, wherein the at least one processor is further configured to:

select a second point on the three-dimensional reference data;

align, on the three-dimensional reference data, a third frame obtained by scanning a third region of the object corresponding to the second point;

align, on the three-dimensional reference data, a fourth frame obtained by scanning a fourth region of the object, at least a portion of the fourth region overlapping the third region; and obtain the three-dimensional data by merging the third frame with the fourth frame based on an overlapping portion between the third region and the fourth region.

14. The device of claim 12, further comprising a user inputter configured to receive a user input, wherein the at least one processor is further configured to select the first point on the three-dimensional reference data based on the user input or select the first point on the three-dimensional reference data automatically.

15. The devices of claim 12, wherein the at least one processor is further configured to:

perform first segmentation on the volumetric metric obtained by computed tomography (CT) or magnetic resonance imaging (MRI) to obtain the three-dimensional reference data;

identify a region corresponding to a plurality of teeth included in the object by performing second segmentation on the three-dimensional reference data; and select a point corresponding to one tooth from among a plurality of teeth included in the object as the first point on the three-dimensional reference data.

16. The device of claim 12, wherein the at least one processor is further configured to:

extract a plurality of apexes on the three-dimensional reference data based on the first point;

extract, from the first frame, a plurality of corresponding points respectively corresponding to the plurality of apexes; and align the first frame on the three-dimensional reference data, based on a difference of distance values between the plurality of apexes and the plurality of corresponding points.

17. The devices of claim 11, wherein the display is configured to display the three-dimensional data on an object image generated from the three-dimensional reference data.

18. A computer-readable recording medium having recorded thereon a program comprising at least one instruction for executing a method of obtaining three-dimensional data with respect to an object, wherein the method of obtaining the three-dimensional data comprises:

obtaining three-dimensional reference data with respect to the object, the three-dimensional reference data being surface data of the object extracted from volumetric data obtained by computed tomography (CT) or magnetic resonance imaging (MRI);

aligning, on the three-dimensional reference data, a first frame obtained by scanning a first region of the object using an optical three-dimensional scanner;

aligning, on the three-dimensional reference data, a second frame obtained by scanning a second region of the object using the optical three-dimensional scanner based on a three-dimensional coordinate value of the aligned first frame, at least a portion of the second region overlapping the first region; and obtaining the three-dimensional data by merging the first frame with the second frame based on an overlapping portion between the first region and the second region.

* * * * *